US005821104A

United States Patent [19]
Holm et al.

[11] Patent Number: 5,821,104
[45] Date of Patent: Oct. 13, 1998

[54] TRIPEPTIDYL AMINOPEPTIDASE

[75] Inventors: Kaj Andre Holm, Roskilde; Grethe Rasmussen, Copenhagen NV; Torben Halkier, Frederiksberg C; Jan Lehmbeck, Vekso, all of Denmark

[73] Assignee: Novo Nordisk A/S, Bagsvaerd, Denmark

[21] Appl. No.: 821,119

[22] Filed: Mar. 19, 1997

Related U.S. Application Data

[63] Continuation-in-part of PCT/DK95/00446, Nov. 8, 1995.

[30]       Foreign Application Priority Data

Nov. 8, 1994 [DK]   Denmark ................................... 1288/94
Dec. 22, 1994 [DK]   Denmark ................................... 1470/94

[51] Int. Cl.$^6$ .............................. C12N 9/62; C12N 15/57; C12N 15/11; C12N 15/80
[52] U.S. Cl. ..................... 435/225; 435/69.1; 435/252.3; 435/254.3; 435/172.3; 435/320.1; 536/23.2
[58] Field of Search ..................................... 435/219, 223, 435/225, 69.1, 172.3, 320.1, 252.3, 254.3; 536/23.2

[56]               References Cited

U.S. PATENT DOCUMENTS 5,616,485   4/1997   Hadary et al. ............................. 435/220

FOREIGN PATENT DOCUMENTS 0440303   8/1991   European Pat. Off. .

WO 92/16642   10/1992   WIPO .
WO 92/17512    6/1995   WIPO .

OTHER PUBLICATIONS

Butler, et al., Applied And Environmental Microbiology, vol. 61, No. 8, pp. 3145–3150 (1995).
Lees, et al., Chemical Abstract, vol. 113, No. 15, Abstract 128464 (Oct. 8, 1990).
Tsyperovych, et al., Ukrainian Biochemical Journal System of Aminopeptidases from *Aspergillus flavus*, vol. 49 No. 1, pp. 101–105, (1977).
Krieger, et al., FEBS Letters vol. 352, pp. 385–388 (1994).
Balow, et al., Biological Chemistry, vol. 258, No. 19, pp. 11622–11628 (Oct. 10, 1983).
McDermott et al., Biochemical Society Transactions, vol. 18, p. 667, (1990).
Watanabe, Y., et al., Biochemistry International, vol. 27, "Acidic tripeptidyl aminopeptidase in rat liver tritosomes: partial purification and determination of its primary substrate specificity", pp. 869–877, 1992.

*Primary Examiner*—Robert A. Wax
*Assistant Examiner*—William W. Moore
*Attorney, Agent, or Firm*—Steve T. Zelson; Elias J. Lambiris

[57]               ABSTRACT

The present invention relates to a tripeptidyl aminopeptidase, a DNA construct encoding the tripeptidyl aminopeptidase, a method of producing tripeptidyl aminopeptidase and methods of reducing the tripeptidyl aminopeptidase production in cells in which tripeptidyl aminopeptidase activity is undesirable.

20 Claims, 7 Drawing Sheets

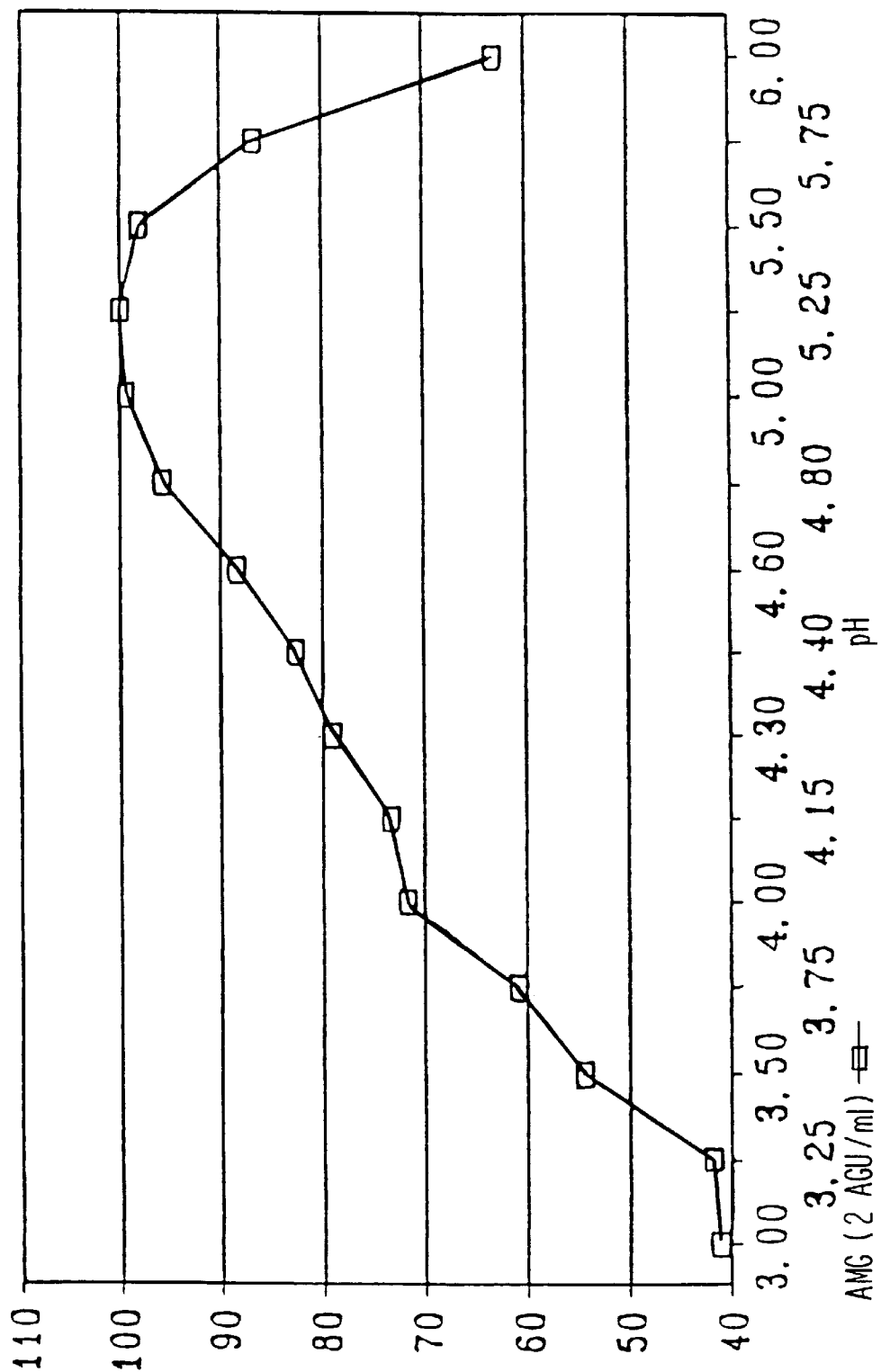

FIG. 2A

| | |
|---|---:|
| A TG TT CT TC AG TC GT GG AG CG CT TT CG CT CG CA GT GC TT TC AC TG CT CA GC TC CT CC GC C<br>M   F   F   S   R   G   A   L   S   L   A   V   L   S   L   L   S   S   S   A | 60 |
| G CA GG GG AG GC TT TT GA GA AG CT GT CT GC CG TT CC AA AG GG AT GG CA CT AT TC TA GT AC C<br>A   G   E   A   F   E   K   L   S   A   V   P   K   G   W   H   Y   S   S   T | 120 |
| C CT AA AG GC AA CA CT GA GG TT TG TC TG AA GA TC GC CC TC GC GC AG AA GG AT GC TG CT GG G<br>P   K   G   N   T   E   V   C   L   K   I   A   L   A   Q   K   D   A   A   G | 180 |
| T TC GA AA AG AC CG TC TT GG AG AT GT CG GA TC CC GA CC AC CC CA GC TA CG GC CA GC AC TT C<br>F   E   K   T   V   L   E   M   S   D   P   D   H   P   S   Y   G   Q   H   F | 240 |
| A CC AC CC AC GA CG AG AT GA AG CG CA TG CT TC TT CC CA GA GA TG AC AC CG TT GA TG CC GT T<br>T   T   H   D   E   M   K   R   M   L   L   P   R   D   D   T   V   D   A   V | 300 |
| C GA CA AT GG CT CG AA AA CG GC GG CG TG AC CG AC TT TA CC CA GG AT GC CG AC TG GA TC AA C<br>R   Q   W   L   E   N   G   G   V   T   D   F   T   Q   D   A   D   W   I   N | 360 |
| T TC TG TA CT AC CG TC GA TA CC GC GA AC AA AC TC TT GA AT GC CC AG TT CA AA TG GT AC GT C<br>F   C   T   T   V   D   T   A   N   K   L   L   N   A   Q   F   K   W   Y   V | 420 |
| A GC GA TG TG AA GC AC AT CC GC CG TC TC AG AA CA CT GC AG TA CG AC GT CC CC GA GT CG GT C<br>S   D   V   K   H   I   R   R   L   R   T   L   Q   Y   D   V   P   E   S   V | 480 |
| A CC CC TC AC AT CA AC AC CA TC CA AC CG AC CA CC CG TT TT GG CA AG AT TA GC CC CA AG AA G<br>T   P   H   I   N   T   I   Q   P   T   T   R   F   G   K   I   S   P   K   K | 540 |
| G CC GT TA CC CA CA GC AA GC CC TC CC AG TT GG AC GT GA CC GC CC TT GC TG CC GC TG TC GT T<br>A   V   T   H   S   K   P   S   Q   L   D   V   T   A   L   A   A   A   V   V | 600 |
| G CA AA GA AC AT CT CG CA CT GT GA TT CT AT CA TT AC CC CC AC CT GT CT GA AG GA GC TT TA C<br>A   K   N   I   S   H   C   D   S   I   I   T   P   T   C   L   K   E   L   Y | 660 |
| A AC AT TG GT GA TT AC CA GG CC GA TG CA AA CT CG GG CA GC AA GA TC GC CT TC GC CA GC TA T<br>N   I   G   D   Y   Q   A   D   A   N   S   G   S   K   I   A   F   A   S   Y | 720 |
| C TG GA GG AG TA CG CG CG CT AC GC TG AC CT GG AG AA CT TT GA GA AC TA CC TT GC TC CC TG G<br>L   E   E   Y   A   R   Y   A   D   L   E   N   F   E   N   Y   L   A   P   W | 780 |
| G CT AA GG GC CA GA AC TT CT CC GT TA CC AC CT TC AA CG GC GG TC TC AA TG AT CA GA AC TC C<br>A   K   G   Q   N   F   S   V   T   T   F   N   G   G   L   N   D   Q   N   S | 840 |

```
TCGTCCGATAGCGGTGAGGCCAACCTGGACCTGCAGTACATTCTTGGTGTCAGCGCTCCA    900
 S  S  D  S  G  E  A  N  L  D  L  Q  Y  I  L  G  V  S  A  P

CTGCCCGTTACTGAATTCAGCACCGGAGGCCGTGGTCCCCTCGTTCCTGATCTGACCCAG    960
 L  P  V  T  E  F  S  T  G  G  R  G  P  L  V  P  D  L  T  Q

CCGGATCCCAACTCTAACAGCAATGAGCCGTACCTTGAGTTCTTCCAGAATGTGTTGAAG   1020
 P  D  P  N  S  N  S  N  E  P  Y  L  E  F  F  Q  N  V  L  K

CTCGACCAGAAGGACCTCCCCCAGGTCATCTCGACCTCCTATGGAGAGAACGAACAGGAA   1080
 L  D  Q  K  D  L  P  Q  V  I  S  T  S  Y  G  E  N  E  Q  E

ATCCCCGAAAAGTACGCTCGCACCGTCTGCAACCTGATCGCTCAGCTTGGCAGCCGCGGT   1140
 I  P  E  K  Y  A  R  T  V  C  N  L  I  A  Q  L  G  S  R  G

GTCTCCGTTCTCTTCTCCTCCGGTGACTCTGGTGTTGGCGAGGGCTGCATGACCAACGAC   1200
 V  S  V  L  F  S  S  G  D  S  G  V  G  E  G  C  M  T  N  D

GGCACCAACCGGACTCACTTCCCACCCCAGTTCCCCGCCGCTTGCCCGTGGGTCACCTCC   1260
 G  T  N  R  T  H  F  P  P  Q  F  P  A  A  C  P  W  V  T  S

GTCGGCGCCACCTTCAAGACCACTCCCGAGCGCGGCACCTACTTCTCCTCGGGCGGTTTC   1320
 V  G  A  T  F  K  T  T  P  E  R  G  T  Y  F  S  S  G  G  F

TCCGACTACTGGCCCCGTCCCGAATGGCAGGATGAGGCCGTGAGCAGCTACCTCGAGACG   1380
 S  D  Y  W  P  R  P  E  W  Q  D  E  A  V  S  S  Y  L  E  T

ATCGGCGACACTTTCAAGGGCCTCTACAACTCCTCCGGCCGTGCTTTCCCCGACGTCGCA   1440
 I  G  D  T  F  K  G  L  Y  N  S  S  G  R  A  F  P  D  V  A

GCCCAGGGCATGAACTTCGCCGTCTACGACAAGGGCACCTTGGGCGAGTTCGACGGCACC   1500
 A  Q  G  M  N  F  A  V  Y  D  K  G  T  L  G  E  F  D  G  T

TCCGCCTCCGCCCCGGCCTTCAGCGCCGTCATCGCTCTCCTGAACGATGCCCGTCTCCGC   1560
 S  A  S  A  P  A  F  S  A  V  I  A  L  L  N  D  A  R  L  R

GCCGGCAAGCCCACTCTCGGCTTCCTGAACCCCTGGTTGTACAAGACCGGCCGCCAGGGT   1620
 A  G  K  P  T  L  G  F  L  N  P  W  L  Y  K  T  G  R  Q  G

CTGCAAGATATCACCCTCGGTGCTAGCATTGGCTGCACCGGTCGCGCTCGCTTCGGCGGC   1680
 L  Q  D  I  T  L  G  A  S  I  G  C  T  G  R  A  R  F  G  G

GCCCCTGACGGTGGTCCCGTCGTGCCTTACGCTAGCTGGAACGCTACCCAGGGCTGGGAT   1740
 A  P  D  G  G  P  V  V  P  Y  A  S  W  N  A  T  Q  G  W  D

CCCGTCACTGGTCTCGGAACTCCCGATTTCGCCGAGCTCAAGAAGCTTGCCCTTGGCAAC   1800
 P  V  T  G  L  G  T  P  D  F  A  E  L  K  K  L  A  L  G  N

TAA 1803
```

```
Consensus   M       S   GA     SLAVLSLL   S   A  E  F
                        10             20          30
A. oryzae   M F - - - F S R G A - L S L A V L S L I S S S A A G E A F   26
A. niger    M L S S L L S Q G A A V S L A V L S L D P S P V A A E L F   30

Consensus   KLS  VP GW Y      P GN       L  IAL  Q
                       40              50           60
A. oryzae   K L S A V P K G W H Y S S T K G N T E V Q L K I A L A Q   56
A. niger    K L S G V P N G W R Y A N N E Q G N E V I R L Q I A L Q Q   60

Consensus   D  AGFE   V   MS P H   YG HF  THDE
                       70              80           90
A. oryzae   D A A G F E K T V L E M S D D H P S Y Q H F T T H D E   86
A. niger    D V A G F E Q A V M D M S T G H A D Y G H H F R T H D E   90

Consensus   KRMLLP     VD VR WLE    GV        D
                       100            110         120
A. oryzae   K R M L L P R D D T V D A V R Q W L E N G V T D F T D D   116
A. niger    K R M L L P S E T A V D S V R D W L S A G V H N I Q V D   120

Consensus   DW  F  TTV   AN LL  A  FKWYVSD  KH
                       130            140         150
A. oryzae   D W I N F C T T V D T A N K L D N A Q F K W Y V S D Y K H   146
A. niger    D W V K F H T T V N K A N A L D D L D F K W Y V S D A K H   150

Consensus   RRLRTLQY   P        HIN  IQPTTRFG
                       160            170         180
A. oryzae   R R L R T L Q Y D V P E S V T P H I N T I Q P T T R F G K   176
A. niger    R R L R T L Q Y S I P D A L V S H I N N I Q P T T R F G Q   180

Consensus      P  A    SKP   DT L   AA   AN  S
                       190            200         210
A. oryzae   S P K K A V T H S K P S Q L V T A L A A V V A K N L S   206
A. niger    Q P N R A T M R S K P K H A D E T I L T A A T L A Q T S   210

Consensus   CDSIITP  CLK  LYNIGDYQAD    SGSKI
                       220            230         240
A. oryzae   C D S I I T P T C L K E L Y N I G D Y Q A D A N S G S K I   236
A. niger    C D S I I T P H C L K Q L Y N I G D Y Q A D P K S G S K I   240

Consensus   FASYLEEYARYADLE  FE    LAP  A  GQN
                       250            260         270
A. oryzae   F A S Y L E E Y A R Y A D L E N F E N L A P W A K G Q N   266
A. niger    F A S Y L E E Y A R Y A D L E R F E Q L A P N A I G Q N   270

Consensus   S V   FNGGLNDQ  SSSDSGEANLDLQYIL
                       280            290         300
A. oryzae   S V T T F N G G L N D Q N S S S D S G E A N L D L Q Y I L   296
A. niger    S V V Q F N G G L N D Q L S S S D S G E A N L D L Q Y I L   300

Consensus   VSAP  P  TE  STGGRG  LVPDL   PDPN
                       310            320         330
A. oryzae   V S A P L P V T E F S T G G R G H L V P D L T Q P D P N S   326
A. niger    V S A P V P I T E Y S T G G R G H L V P D L S S P D P N D   330
```

FIG. 3B

```
Consensus    S N E P Y L   F   Q     L K L       D L P Q V I S T S Y G
                         340           350               360
A. oryzae    S N E P Y L E F F Q N V L K D Q H D L P Q V I S T S Y G  356
A. niger     S N E P Y L D E L G I L K D N N S D L P Q V I S T S Y G  360

Consensus      E Q   I P     Y A R T V C N L   A Q L G S R G V S V   F
                         370           380               390
A. oryzae    N E Q E I P E Y A R T V C N L I A Q L G S R G V S V L F  386
A. niger     D E Q T I P V P Y A R T V C N L Y A Q L G S R G V S V L F 390

Consensus    S G D S G V G     C   T N D G T N R T H F P P Q F P A   C
                         400           410               420
A. oryzae    S G D S G V G E G C M T N D G T N R T H F P P Q F P A A C  416
A. niger     S G D S G V G A A C L T N D G T N R T H F P P Q F P A S C  420

Consensus    W V T S V G A T   K T   P E         F S S G G F S D   W P
                         430           440               450
A. oryzae    W V T S V G A T F K T T P E R G T Y F S S G G F S D Y W P  446
A. niger     W V T S V G A T S K T S P E Q A V S F S S G G F S D L W P  450

Consensus    P   Q     A V     Y L         G     F   G L   N   S G R
                         460           470               480
A. oryzae    P E W Q D E A V S S Y L E T - I D T F H G L Y N S S G R  475
A. niger     P S Y Q H A A V Q T Y L T K H L G N R S G L F N A S G R  480

Consensus    F P D V   A Q G   N   A V Y D K G   L G   F D G T S   S A
                         490           500               510
A. oryzae    F P D V A A Q G M N F A V Y D K G T L G F F D G T S A S A  505
A. niger     F P D V S A Q G V N Y A V Y D K G N L G Q F D G T S C S A  510

Consensus      F S   V I A L L N D A R L R A G     P     G F L N P   L Y
                         520           530               540
A. oryzae    A F S A V I A L L N D A R L R A G K F T G F L N P V L Y  535
A. niger     T F S G V I A L L N D A R L R A G D F V G F L N P F L Y  540

Consensus      G         L   D I     G   S     G C     G R   R F G G   P
                         550           560               570
A. oryzae    T G R Q - - G L Q D I T L G A S I G Q T G H A R F G G A P  563
A. niger     V G S E K G A L N D T V N G S V G G G G H N R F G G T P  570

Consensus    G   P V V P   A S W N A T   G W D P V   G L G T P D F A
                         580           590               600
A. oryzae    G G P V V P Y A S W N A T G G W D P V T G L G T P D F A E  593
A. niger     G S P V V P F A S W N A T T G W D P V S G L G T P D F A K  600

Consensus    K   A L G         N
                         610
A. oryzae    K K L A L G - - - N                                       600
A. niger     K G V A L G E E G N                                       611
```

TRIPEPTIDYL AMINOPEPTIDASE

CROSS-REFERENCE TO RELATED APPLICATIONS

This application is a continuation-in-part of PCT/DK95/00446 filed Nov. 8, 1995, which claims priority of Danish application serial nos. 1288/94 filed Nov. 8, 1994 and 1470/94 filed Dec. 22, 1994, the contents of which applications are fully incorporated herein by reference.

FIELD OF THE INVENTION

The present invention relates to a tripeptidyl aminopeptidase (TPAP), a DNA construct encoding the TPAP, a method of producing TPAP and methods of reducing the TPAP production in cells in which TPAP activity is undesirable.

BACKGROUND OF THE INVENTION

Tripeptidyl aminopeptidases (TPAPs) are enzymes capable of cleaving tripeptide fragments from unsubstituted N-termini of peptides, oligopeptides, or proteins. TPAP substrate specificities range from broad to narrow.

TPAPs of animal origin have been previously reported. For instance, Doebber et al. (1978, Endocrinology 103:1794–1804), disclose a TPAP isolated from bovine pituitary gland, which was shown to cleave tripeptides from the N-terminus of bovine growth hormone. In *Mammalian Proteases, Vol. 2, Exopeptidases* (J. K. McDonald and A. J. Barrett, eds., Academic Press, London, UK, 1986) tripeptidyl aminopeptidases are disclosed which had been isolated from pregnant hog ovaries and hog spleen.

A bacterial TPAP was isolated from *Streptomyces lividans* 66 by Krieger et al. (1994, FEBS Lett. 352:385–388). The gene encoding said peptidase and the deduced amino acid sequence were subsequently reported by Butler et al. (1995, Applied and Environmental Microbiology 61:3145–3150). The peptidase was characterized as a serine protease with a pH optimum of between 7.5 and 8.5.

It is well known that the stability of microbially produced products, such as heterologous enzymes and other proteins, may be influenced by factors such as the method of purification and/or the origin or microbial producer of the product. Reduced stability of a microbial protein product may be due to physicochemically damaging exposure to heat, light or other environmental conditions, or may be due to inherent properties of the primary structure of the product. Therefore, the co-presence of even trace amounts of contaminating proteolytic activity in a protein product may result in a significantly reduced stability of said product. Often, however, it is not possible to exactly identify the basis for reduced stability.

SUMMARY OF THE INVENTION

The present inventors have now surprisingly found that various fungal species produce TPAP and that protein products purified from these organisms may contain minor amounts of TPAP which in some cases have been found to lead to a reduced stability of these products. The present inventors have succeeded in isolating and characterizing said TPAP. It has been established that the TPAP is capable of non-specifically cleaving tripeptides from the unsubstituted N-termini of protein products, which in some instances may be desirable, and not in other instances, e.g., when it is a contaminant in the purification of a protein of interest resulting in a reduced stability of said protein product.

Accordingly, one objective of the present invention is to provide a substantially pure tripeptidylpeptidase which may be used for cleaving peptide or protein sequences of interest. Another purpose is to provide a method of producing protein products essentially free from TPAP, in particular, products which are substrates for TPAP and which have a reduced stability in the presence of TPAP.

In a first general aspect, the present invention relates to an isolated TPAP of fungal origin. In particular, the TPAP may be obtainable from strains of the fungal genus Aspergillus. Other aspects of the invention relate to TPAP, identified by specific amino acid and/or DNA sequence information and/or by specific enzyme protein characteristics, to DNA constructs encoding the TPAP and to a DNA construct comprising a nucleotide sequence which is sufficiently complementary to the DNA sequence encoding TPAP, such that hybridization to said sequence will inhibit or significantly reduce the TPAP producing capability of a given host cell.

In a further important aspect, the invention relates to a method of reducing the TPAP production from a TPAP producing cell, wherein a DNA sequence present in said cell and necessary for the expression of TPAP is modified or inactivated so as to result in a reduced TPAP production from said cell.

DEFINITIONS

In the present context, the term "TPAP" is intended to indicate an aminopeptidase which cleaves tripeptides from the N-terminus of a peptide or protein sequence, such as an extended amino acid sequence found in a prohormone or a proenzyme. Expressed in a general manner, the TPAP is capable of cleaving the tripeptide XYZ from the unsubstituted N-terminal amino group of a peptide or protein, in which each of X, Y, and Z represents any amino acid residue selected from Ala, Arg, Asn, Asp, Cys, Gln, Glu, Gly, His, Ile, Leu, Lys, Met, Phe, Pro, Ser, Thr, Trp, Tyr and Val. In the TPAP substrate X, Y and Z may each be different, two of X, Y and Z may be identical, or X, Y and Z may all be identical. It will be understood that the tripeptide aminopeptidases encoded by the isolated nucleic acid sequences of the present invention are unspecific as to the amino acid sequence of the tripeptide to be cleaved. Example 7 provides specific examples of tripeptide products obtained from the cleavage by TPAP of naturally occurring peptides and proteins.

The term "obtainable" as used herein refers to the source of DNA sequences in the DNA constructs of the invention. Said term is intended to indicate that the DNA sequence in question may be isolated from nucleic acid material, such as DNA or RNA, of the relevant organism or may be prepared on the basis of such material. For instance, the DNA sequence may be isolated from a genomic or cDNA library prepared from the organism using procedures known in the art, or may be prepared on the basis of such material.

Analogously, when used in connection with the TPAP protein product of the invention, the term "obtainable" is intended to indicate that the TPAP protein may be recovered from the organism of interest or may be encoded by a DNA sequence obtainable from said organism and recovered from an organism expressing said DNA sequence.

The term "isolated" as used herein refers to a nucleic acid sequence or a polypeptide which is essentially free of other nucleic acid or polypeptide sequences, respectively, e.g., at least about 20% pure, preferably at least about 40% pure, more preferably at least about 60% pure, even more preferably at least about 80% pure, and most preferably at least about 90% pure as determined, for example, by agarose or SDS-polyacrylamide electrophoresis.

For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, or synthetic origin, or any combinations thereof.

The TPAP of the invention is preferably provided in an isolated and substantially pure form, e.g. at least 90% pure, and optimally at least 95% pure.

BRIEF DESCRIPTION OF THE FIGURES

FIG. 1 shows the effect of pH on *Aspergillus niger* TPAP activity.

FIG. 2 shows the nucleic acid sequence and the deduced amino acid sequence of the *Aspergillus oryzae* ATCC 20386 tripeptide aminopeptidase I (SEQ ID Nos. 18 and 19).

FIG. 3 shows a sequence comparison of the *Aspergillus oryzae* ATCC 20386 tripeptide aminopeptidase I and *Aspergillus niger* tripeptide aminopeptidase (SEQ ID No. 17).

DETAILED DISCLOSURE OF THE INVENTION

The TPAP of the invention

Figure 4:
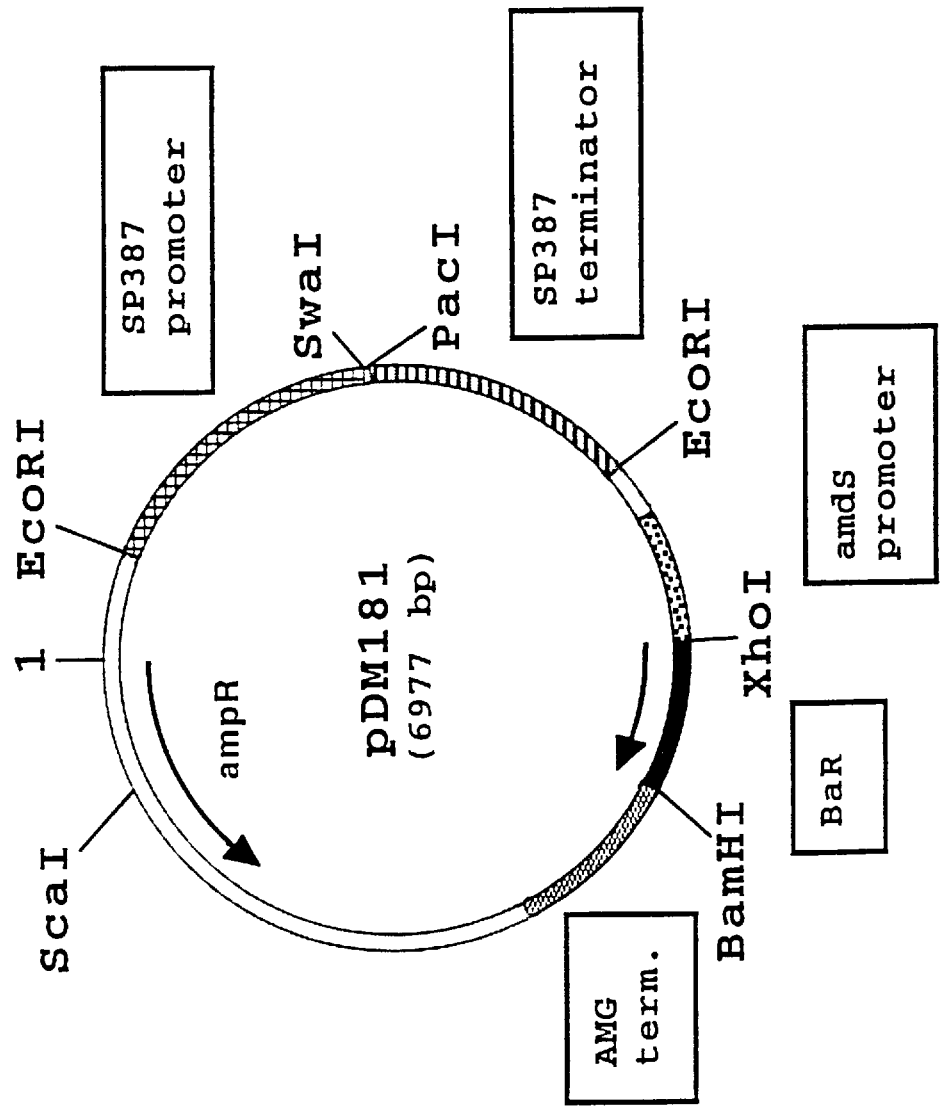
FIG. 4 shows a restriction map of pDM181.

In the course of the research leading to the present invention two different TPAPs were isolated and characterized; one from a strain of *A. niger*, another from a strain of *A. oryzae*. The two TPAPs are contemplated to be representative examples of a generally novel class of tripeptidyl aminopeptidases.

Thus, one aspect of the invention relates to a TPAP which is encoded by a nucleic acid sequence comprising:

(a) the complete DNA sequence encoding TPAP shown in SEQ ID No. 16, or its complementary strand;

(b) the complete DNA sequence encoding the TPAP constituted by the N-terminal TPAP encoding sequence in DSM 11128 and the C-terminal encoding sequence in DSM 11129;

(c) a nucleic acid sequence which hybridizes to an oligonucleotide probe prepared on the basis of said sequence, or on the basis of the amino acid sequence shown in SEQ ID No. 17, and which encodes a polypeptide with TPAP activity;

(d) an allelic form of (a), (b) or (c); and (e) a fragment of (a), (b), (c) or (d).

In a preferred embodiment, the polypeptide with TPAP activity is encoded by a nucleic acid sequence selected from the group consisting of: (a) at least one of, but preferably two or more of, the partial DNA sequences shown in SEQ ID Nos. 1, 2 and 3, or the respective complementary strand; (b) a nucleotide sequence which hybridizes to an oligonucleotide probe prepared on the basis of any of the DNA sequences shown in SEQ ID Nos. 1, 2, and 3, or on the basis of any of the amino acid sequences shown in SEQ ID Nos.

4–14, and which encodes a TPAP; (c) an allelic form of (a) or (b); and (d) a fragment of (a), (b) or (c).

A more detailed explanation of the nucleotide sequence of (c) and (b), respectively, in the two preceding paragraphs, is given further below in the section entitled The DNA construct and vector of the invention.

In another aspect, the invention relates to an isolated TPAP which has one or more of the following characteristics:

(a) capability to cleave the substrate Phe-Pro-Ala-pNA, (b) a molecular weight of about 65 kDa (determined as described by Laemmli, U.K., 1970, Nature 227:680–685), (c) a pI in the range of 4–6, (d) an optimum activity in the pH range of about 5.0–7.5, (e) immunological cross-reactivity with the purified *A. niger* TPAP or the purified *A. oryzae* TPAP, and (f) an N-terminal sequence comprising: Ala-Xaa(1)-Asn-Xaa(2)-Ser-His-Cys-Asp-Ser-Ile-Ile-Thr-Pro-Xaa(3)-Cys-Leu-Lys-Xaa(4)-Leu-Tyr-Asn-Ile-Gly-Asp-Tyr-Gln-Ala-Asp-Xaa(5)-Xaa(6) (SEQ ID No. 15), in which any one of Xaa(1), Xaa(2), Xaa(3), Xaa(4), Xaa(5) and Xaa(6) may be different or identical and selected from any of the naturally occurring amino acid residues.

Preferably, Xaa(1) is Lys or Gln, Xaa(2) is Ile or Thr, Xaa(3) is Pro or His, Xaa(4) is Glu or Gln, Xaa(5) is Pro or Ala, and Xaa(6) is Lys or Asn.

Antibodies to be used in determining immunological cross-reactivity may be prepared by use of the isolated TPAP. More specifically, antiserum against the enzyme of the invention may be raised by immunising rabbits or rodents, such as rats and mice, according to the procedure described by N. Axelsen, et al. (*A Manual of Quantitative Immunoelectrophoresis*, Chapter 23, Blackwell Scientific Publications, Oxford, UK, 1973) or A. Johnstone and R. Thorpe (*Immunochemistry in Practice*, pp. 27–31, Blackwell Scientific Publications, Oxford, UK, 1982). Purified immunoglobulins may be obtained from the antisera, for example, by ammonimum sulfate salt [$(NH_4)_2SO_4$] precipitation, followed by dialysis and ion exchange chromatography, e.g. on DEAE-Sephadex™ (Pharmacia Biotech, Piscataway N.J., USA). Immunochemical characterization of proteins may be done either by Outcherlony double-diffusion analysis (O. Outcherlony in *Handbook of Experimental Immunology*, D. M. Weir, ed., Blackwell Scientific Publications, Oxford, UK, 1967, pp. 655–706), by crossed immunoelectrophoresis (N. Axelsen et al., supra, Chapters 3 and 4), or by rocket immunoelectrophoresis (N. Axelsen et al., supra, Chapter 2).

In one embodiment the TPAP of the invention comprises at least one of the following characteristics: an amino acid sequence as shown in the partial amino acid sequences in SEQ ID Nos. 4–9 or the complete amino acid sequence shown in SEQ ID No. 17, a pH optimum of about 5.0–5.5 and a pI of about 5.1 or 5.2.

The TPAP which is encoded by the following was isolated from a protein product produced by a strain of *A. niger* (cf. Example 1): a DNA sequence comprising at least one of the sequences shown in SEQ ID Nos. 1, 2 and 3, the DNA sequence harbored in DSM 9570, the complete DNA sequence shown in SEQ ID No. 16, or the sequence obtained by combining the DNA sequence encoding the N-terminal region of TPAP in DSM 11128 with the DNA sequence encoding the C-terminal region of TPAP in DSM 11129; an amino acid sequence comprising any of the peptides shown in SEQ ID Nos. 4–9 or the complete amino acid sequence shown in SEQ ID No. 17. The TPAP comprising any of the peptides in SEQ ID Nos. 10–14 was isolated from a strain of *A. oryzae* (cf. Example 11).

It is presently believed that a TPAP belonging to the generally novel class of tripeptidyl aminopeptides defined herein may be of any origin, including animal or plant origin, but preferably is of microbial, i.e. bacterial or fungal, origin. As far as the present inventors are aware, the present disclosure is the first report of a TPAP of fungal origin. The TPAP of the invention may be purified from strains which are natural TPAP producers, or may be more conveniently produced by means of recombinant DNA techniques as a homologous or heterologous gene product as will be further explained below.

In particular, the TPAP of the invention may be obtainable from a strain of Aspergillus, such as a strain of *A. oryzae, A. niger, A. japonicus, A. aculeatus, A. nidulans* or *A. foetidus* or a strain of Trichoderma, e.g. *T. viride, T. reesei, T. longibrachiatum* or *T. harzianum*, or a species of Fusarium, e.g. *F. oxysporum, F. graminearum, F. venenatum* or *F. solani*, or a strain of Thermomyces, e.g. *T. lanuginosus* or *T. insolens*.

In another embodiment the TPAP of the invention comprises at least one of the partial amino acid sequences shown in SEQ ID Nos. 10–14 and/or has a pH optimum in the range of about 5.5–7.5 and/or a pI of about 4.5. Said TPAP is preferably of fungal origin and may be obtainable from a strain of Aspergillus, such as a strain of *A. oryzae, A. niger, A. japonicus* or *A. foetidus*.

While the presence of TPAP in protein products susceptible to TPAP hydrolysis may be considered undesirable due to the resultant reduced stability of said products, the use of the purified TPAP of the invention for controlled destabilization of protein products may be advantageous. For instance, it is contemplated that the purified TPAP of the invention may be used for the deactivation of enzymes after they have exerted their desired effect, and thus function as a "killer enzyme". Such deactivation is conventionally accomplished by thermoinactivation, but the process may also result in a loss of activity of the protein of interest. In some cases, it is necessary to remove the undesirable enzyme activity through additional purification procedures. Therefore, use of TPAP for the inactivation of thermophilic enzymes may be particularly advantageous.

An example of such use of TPAP is in the deactivation of AMG (amyloglucosidase), which is used for starch liquefaction. In current practice, the enzyme is deactivated by heating the reaction mixture to high temperatures (80°–85° C.). The equivalent may be achieved at lower temperatures by first adding TPAP, preferably in a batch process after AMG has hydrolyzed dextrins to glucose. Complete inactivation of AMG would then only require increasing the temperature to about 66° C. for a short period.

Another example where TPAP inactivation of AMG may be desirable is in the fermentation of beer, such as low calorie beer. In the normal beer fermentation procedure, AMG is inactivated by pasteurization. It is contemplated that by adding TPAP to reduce the thermostability of the used AMG, a lower temperature would be required for pasteurization of the beer product. This treatment could result in improved organoleptic characteristics of beer.

Furthermore, a purified TPAP of the invention may be useful for a number of purposes in which a specific cleavage of tripeptide sequences is desirable. For instance, there are some proteins or peptides which are synthesized in the form of inactive precursors comprising a number of additional amino acid residues at the N-terminal of the mature protein. TPAP could provide the necessary post-translational processing to activate such precursor proteins.

The DNA construct and vector of the invention

In accordance with a still further aspect, the invention relates to a DNA construct encoding a TPAP, which comprises:

(a) the nucleic acid sequence shown in SEQ ID No. 16;

(b) the complete DNA sequence encoding the TPAP constituted by the N-terminal TPAP encoding sequence in DSM 11128 and the C-terminal encoding sequence in DSM 11129;

(c) a nucleic acid sequence which hybridizes to an oligonucleotide probe prepared on the basis of said sequence, or on the basis of the amino acid sequence shown in SEQ ID No. 17, and which encodes a polypeptide with TPAP activity;

(d) an allelic form of (a), (b) or (c);

(e) a fragment of (a), (b), (c) or (d); and (f) a nucleotide sequence complementary to the nucleotide sequence of (a), (b), (c), (d) or (e).

In a preferred embodiment, the DNA construct is encoded by a nucleic acid sequence selected from the group consisting of:

(a') any of the nucleic acid sequences shown in SEQ ID Nos. 1, 2 and 3;

(b') a nucleic acid sequence which hybridizes to an oligonucleotide probe prepared on the basis of any of the sequences shown in SEQ ID Nos. 1, 2 and 3, or on the basis of any of the amino acid sequences shown in SEQ ID Nos. 4–14, and which encodes a tripeptidyl aminopeptidase;

(c') an allelic form of (a') or (b');

(d') a fragment of (a'), (b') or (c'); and (e') a nucleotide sequence complementary to the nucleotide sequence of (a'), (b'), (c') or (d').

A DNA construct of the invention based on nucleotide sequences of (a)–(e) and (a')–(d'), respectively, of the two preceding paragraphs may be used for the production of TPAP by recombinant DNA methodology known in the art, whereas nucleotide sequence (e) and (d') may be used for reducing the TPAP producing capability of a cell when said production is undesirable.

The nucleotide sequence (c) and (b'), respectively, of the two paragraphs above may be isolated from another or related (e.g., by species or strain) organism, known or contemplated to produce TPAP, on the basis of any of the partial or complete DNA sequences shown in SEQ ID Nos. 1–3 and 16, any of the partial or complete amino acid sequences shown in SEQ ID Nos. 4–14 and 17, the partial TPAP encoding DNA sequence of DSM 9570, or the complete TPAP encoding DNA sequence obtained by combining the N-terminal DNA sequence encoding TPAP present in DSM 11128 with the C-terminal DNA sequence encoding TPAP present in DSM 11129, e.g. by using the procedures described herein.

The nucleotide sequence (f) and (e'), respectively, of the two paragraphs above may be constructed on the basis of any of said nucleic acid or amino acid sequences, including, e.g., sequences in which nucleotide substitutions have been introduced but which do not affect the enzymatic activity. The introduction of such substitutions may be of no consequence or may result in a change in the amino acid sequence from the native protein. Thus, it is possible to generate a TPAP mutant in which the enzymatic activity is the same as the native TPAP but which has physicochemical properties different from the native TPAP. Other examples of possible modifications are insertion of one or more nucleotides into the sequence, addition of one or more nucleotides at either end of the sequence, and deletion of one or more nucleotides at either end or within the sequence.

It will be understood that the DNA sequences shown in SEQ ID Nos. 1–3 and the DNA sequence of DSM 9570 are partial sequences which may be included in and used for isolating an entire TPAP encoding DNA sequence. This may easily be achieved by methods known in the art as illustrated in Example 10. In accordance with the present invention, the nucleic acid sequence shown in SEQ ID No. 16 (in which the coding region is from positions 166 (ATG) to 278, 346 to 11322, and 1394 to 2139 (Stop codon) and there are introns between positions 278–345 and 1323–1393) and the DNA sequence constituted by the N-terminal TPAP encoding sequence in DSM 11128 and the C-terminal encoding sequence in DSM 11129 are intended to include said DNA sequence in its entirety.

The aforementioned hybridization in reference to nucleotide sequences (c) and (b') above is intended to indicate that said sequence hybridizes to a DNA sequence encoding the TPAP or a portion thereof under certain specified conditions which are described in detail in Example 10. Normally, the nucleotide sequences (c) and (b') are highly homologous to the DNA sequence shown in SEQ ID Nos. 1, 2, 3 and 16, or to the TPAP encoding DNA sequence of DSM 9570 and DSM 11128 and DSM 11129.

The DNA sequence homology referred to herein is determined as the degree of identity between two sequences indicating a derivation of the first sequence from the second. The homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711; Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, more preferably at least 97% with the TPAP encoding region of any of the DNA sequences shown in SEQ ID Nos. 1, 2, 3, and 16.

The nucleotide sequences (c) and (b') described above may be a DNA or an RNA sequence.

The nucleic acid sequences (a)–(e) and (a')–(d') of the DNA construct of the invention may be prepared by well-known methods. Thus, the relevant DNA sequence may, for instance, be isolated by establishing a cDNA or genomic library from an organism expected to harbor the sequence, e.g. a cell as described above, and screening for positive clones by conventional procedures. Examples of such procedures are hybridization to suitable oligonucleotide probes in accordance with standard techniques (cf. *Molecular Cloning: A Laboratory Manual*, Sambrook et al., Cold Spring Harbor, N.Y., 1989), and/or selection for clones expressing the relevant activity, and/or selection for clones producing a protein which is reactive with an antibody raised against the relevant enzyme.

A preferred method of isolating a DNA sequence from a cDNA or genomic library is by use of polymerase chain reaction (PCR) techniques using degenerate oligonucleotide probes. For instance, the PCR may be carried out using the techniques described in *PCR Protocols,* 1993, Bruce A. White, ed., Humana Press, Totowa, N.J., or *The Polymerase Chain Reaction,* 1994, Kary B. Mullis, Francois Ferre and Richard A. Gibbs, eds., Birkhaeuser, Boston, Mass.

Alternatively, the DNA sequences (a) and (b) may simply be isolated from DSM 11128 and DSM 11129.

Furthermore, DNA sequences of the DNA construct of the invention, e.g., the complementary nucleotide sequences (f) and (e'), may be synthesized by established techniques, e.g. based on the principles disclosed by Narang, S. A. (1983, Tetrahedron 39:3) and Itakura et al. (1984, Annu. Rev. Biochem. 53:323).

The DNA construct may be of mixed genomic and synthetic, mixed synthetic and cDNA, or mixed genomic and cDNA origin. In accordance with standard techniques, a construct of the invention may be prepared by ligating nucleotide fragments derived from such mixed sources in a manner which will result in a recombinant molecule that encodes the entire TPAP sequence.

It will be understood that a preferred use of any of the nucleotide sequences (a)–(e) and any of the nucleotide sequences (a')–(d') is in the preparation of a recombinant TPAP, whereas a preferred use of either of the nucleotide sequences (f) and (e) is for the reduction of the TPAP producing capability in cells in which it is desirable to enhance the production of protein products sensitive to TPAP destabilization.

Although the nucleotide sequences (f) and (e') may be complementary to the entire TPAP encoding sequence, it is normally sufficient that said sequence is complementary to only part of the TPAP encoding sequence. Expressed in functional terms, the nucleotide sequences (f) and (e') must be sufficiently complementary to a length of the DNA sequence encoding the TPAP to allow a stable hybridization and achieve a reduction or prohibition of the transcription of said DNA. Typically, it is sufficient that the nucleotide sequence (f) and (e') comprises a DNA fragment of at least 17 nucleotides, but preferably, at least 300 nucleotides.

The vector carrying a DNA construct of the invention, preferably a recombinant expression vector, may be any vector which may be conveniently subjected to recombinant DNA procedures. The choice of expression vector will often depend on the host cell into which it is to be introduced. Thus, the vector may be an autonomously replicating vector, i.e. a vector which exists as an extrachromosomal entity, the replication of which is independent of chromosomal replication, such as a plasmid or a bacteriophage. Alternatively, the vector may be one which, when introduced into a host cell, is integrated into the host cell genome and replicated together with the chromosome(s) into which it has been integrated.

In the DNA construct or the vector, the protein coding sequence should be operably connected to a suitable promoter sequence. The promoter may be any DNA sequence which shows transcriptional activity in the host cell of choice and may be derived from genes encoding proteins either homologous or heterologous to the host cell. The promoter may be derived from genes encoding either extracellular or intracellular proteins, such as amylases, glucoamylases, proteases, lipases, cellulases and glycolytic enzymes. Examples of suitable promoters for directing the transcription of the DNA construct of the invention include, but are not limited to, promoters derived from genes for *A. oryzae* TAKA amylase, *Rhizomucor miehei* aspartic proteinase, *A. niger* glucoamylase, *A. niger* neutral α-amylase, *A. niger* acid stable α-amylase, and *Rhizomucor miehei* lipase. Examples of promoters from genes for glycolytic enzymes include, but are not limited to, TPI (triosephosphate isomerase), ADH (alcohol dehydrogenase I), and PGK (3-phosphoglycerate kinase). The promoter may also be a homologous promoter, i.e. derived from a gene native to the host strain being used.

The promoter sequence may be modified with linker sequences for the purpose of introducing specific restriction sites to facilitate ligation of the promoter sequence to the gene of choice or to a selected signal peptide or preregion.

The DNA construct and/or expression vector of the invention may also comprise a suitable terminator sequence, operably connected to the DNA sequence encoding the TPAP and/or a polyadenylation sequence. The terminator and polyadenylation sequences may be derived from the same sources as the promoters. Enhancer sequences may also be inserted into the construct.

The DNA construct and/or vector may further comprise a DNA sequence enabling the vector to replicate in the host cell of interest. Examples of such sequences include, but are not limited to, the origins of replication of plasmids pUC19, pACYC177, pUB110, pE194, pAMB1 and pIJ702.

The DNA construct and/or vector may also comprise a selectable marker. Examples of selection markers include, but are not limited to, amdS or argB, trpC or pyrG; the latter three markers are from *A. nidulans* or *A. niger*.

The procedure used to construct the DNA construct of the invention comprises first ligating the DNA sequences mentioned above to the promoter, the terminator and other elements, respectively. The construct is then inserted into suitable vectors containing the information necessary for replication in the host cell of choice, using techniques which are well known to persons skilled in the art (cf., Sambrook et al., op. cit.).

The cell and a method of producing TPAP of the invention

In one embodiment the cell of the invention, either comprising a DNA construct or an expression vector of the invention as defined above, is used as a host cell in the production of recombinant TPAP of the invention. In this case the DNA construct or expression vector comprises any of the TPAP encoding sequences (a)–(e) or the insert of DSM 11128 or DSM 11129 defined above. The cell may be conveniently transformed with the DNA construct by integrating the DNA construct into the host chromosome, although the DNA construct may also exist as an extrachromosomal entity. Integration is generally considered to be more advantageous because the DNA sequence is more likely to be stably maintained in the cell. Integration of the DNA constructs into the host chromosome may be performed according to conventional methods, e.g. by homologous recombination. Alternatively, the cell may be transformed with an appropriate expression vector for a variety of host cells as described below.

The cell of the invention may be a cell of a higher organism such as a mammal or an insect, but is preferably a microbial cell, e.g. a bacterial or a fungal (including yeast) cell.

Examples of suitable bacteria include, but are not limited to, gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulars, Bacillus lautus, Bacillus thuringiensis* or *Streptomyces lividans* or *Streptomyces murinus*, or gram negative bacteria such as *E. coli*. The transformation of suitable bacteria may be effected by protoplast transformation or by using competent cells in a manner known per se.

A suitable yeast organism may be selected from a species of Saccharomyces or Schizosaccharomyces, e.g. *Saccharomyces cerevisiae*. A suitable filamentous fungus may belong to a species of Aspergillus, e.g. *Aspergillus oryzae, A. nidulans, A. foetidus, A. aculeatus, A. japonicus* or *A. niger*, a species of Trichoderma, e.g. *T. reesei, T. longibrachiatum* or *T. harzianum*, or a species of Fusarium, e.g. *F. oxysporum, F. graminearum, F. venenatum* or *F. solani*. Fungal cells may be transformed by a process involving protoplast formation followed by regeneration of the cell wall in a manner known per se.

In a further aspect the invention relates to a method of producing TPAP, in which the method comprises culturing a cell of the invention as defined above in a suitable culture medium under conditions permitting expression of the TPAP, and recovering the TPAP from the culture. The medium used to cultivate the cells may be any conventional medium suitable for growing the host cell in question. Suitable media are available from commercial suppliers or may be prepared according to published recipes, as in catalogues of the American Type Culture Collection (Bethesda, Md.). It is believed that the presence of protein in the medium may enhance TPAP production.

The TPAP may be recovered from the medium by conventional procedures, including separating the cells from the medium by centrifugation or filtration, disruption of the cells, if necessary, precipitating the proteinaceous components of the supernatant or filtrate by means of a salt, e.g. ammonium sulphate, followed by purification by a variety of chromatographic procedures, such as ion exchange chromatography, affinity chromatography, and the like.

Removal or reduction of TPAP activity

The identification of TPAP as a destabilizing factor in microbially produced protein products may have important consequences for the production of a large number of different protein products. As demonstrated by the present inventors, even minor amounts of TPAP present in a protein product may result in a reduced stability of said product. Accordingly, by the present invention it is possible to construct production strains of commercial value which have a reduced TPAP producing capability.

The reduction of TPAP production or activity from a TPAP producing cell may be conveniently accomplished by modification or inactivation of a DNA sequence present in said cell and necessary for expression of TPAP. The DNA sequence to be modified or inactivated may be, for example, a DNA sequence encoding TPAP or a part thereof essential for exhibiting TPAP activity, or the sequence may have a regulatory function required for the expression of TPAP from a TPAP encoding DNA sequence. An example of a regulatory sequence may be a promoter sequence or a functional part thereof, i.e. a part which is sufficient for affecting expression of TPAP.

The modification or inactivation of the DNA sequence may be performed by subjecting the TPAP producing cell to mutagenesis and selecting for cells in which the TPAP producing capability has been reduced or removed. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells showing a reduced TPAP production.

The modification or inactivation of TPAP production may be accomplished by introduction, substitution or removal of one or more nucleotides in the TPAP encoding sequence or a regulatory element required for the transcription or translation thereof. For example, nucleotides may be inserted or removed so as to result in the introduction of a stop codon, the removal of the start codon or a change of the open reading frame. The modification or inactivation of the TPAP encoding sequence or a regulatory element thereof may be accomplished by site-directed mutagenesis or PCR generated mutagenesis in accordance with methods known in the art. Although, in principle, the modification may be performed in vivo, i.e. directly on the cell expressing the TPAP gene to be modified, it is presently preferred that the modification be performed in vitro as exemplified below.

An example of a convenient way to inactivate or reduce the TPAP production of a host cell of choice is based on techniques of gene replacement or gene interruption. For instance, in the gene interruption method, a DNA sequence corresponding to the endogenous gene or gene fragment of interest is mutagenized in vitro. Said DNA sequence thus encodes a defective gene which is then transformed into the host cell. By homologous recombination the defective gene replaces the endogenous gene or gene fragment. It may be desirable that the defective gene or gene fragment also encodes a marker which may be used for selection of transformants in which the TPAP gene has been modified or destroyed.

Alternatively, the modification or inactivation of the DNA sequence may be performed by established anti-sense techniques using a nucleotide sequence complementary to the TPAP encoding sequence, e.g. the nucleotide sequence (f) described above. More specifically, the TPAP production from a TPAP producing cell may be reduced or eliminated by introducing a nucleotide sequence complementary to the TPAP encoding sequence which may be transcribed in the cell and is capable of hybridizing to TPAP mRNA produced in the cell. Under conditions allowing the complementary anti-sense nucleotide sequence to hybridize to the TPAP mRNA the amount of TPAP translated is thus reduced or eliminated.

The TPAP-deficient mutants so created are particularly useful as host cells for the expression of heterologous proteins. In the present context the term "heterologous proteins" is intended to indicate a protein which is not native to the host cell, a native protein in which modifications have been made to alter the native sequence, or a native protein whose expression is quantitatively altered as a result of a manipulation of the host cell by recombinant DNA techniques.

It is preferred that the TPAP producing cell to be modified in accordance with the present invention is of microbial origin, for example, a fungal strain which is suitable for the production of desired protein products, either homologous or heterologous to the cell. Cells of the fungal genera Aspergillus, Trichoderma and Fusarium are examples of preferred production cells. Accordingly, the cell to be modified in accordance with the present invention is preferably a cell of an Aspergillus species, in particular a cell of *A. niger, A. oryzae, A. japonicus, A. foetidus* or *A. nidulans* or a cell of a Trichoderma species, e.g. *T. reesei, T. longibrachiatum* or *T. harzianum*, or a cell of a Fusarium species, e.g. *F. oxysporum, F. graminearum, F. venenatum* or *F. solani*.

In a specific embodiment of the invention the cell to be modified is from a strain of *A. niger* or *A. oryzae* which is used for the production of enzymes such as AMG.

In a further aspect the invention relates to a method of preparing a product essentially free from TPAP activity, in which the method comprises transforming a host cell suitably modified as described above to exhibit a reduced or no TPAP producing capability with a DNA sequence encoding the protein of interest, culturing the transformed cell under suitable conditions for expression of the protein product, and recovering the product from the culture.

In an alternative aspect the invention relates to a method of preparing a protein product essentially free from TPAP activity, wherein the product is encoded by a DNA sequence present in a TPAP expressing cell. The method comprises modifying or inactivating a DNA sequence present and necessary for the expression of TPAP in said cell as described above, and subsequently culturing the cell under suitable conditions for expression of the product, and recovering the product from the culture.

In a still further aspect the invention relates to a method of preparing a product essentially free from TPAP by fermentation of a TPAP producing cell which also produces the protein product of interest. The method comprises adding an effective amount of an agent capable of inhibiting TPAP activity to the fermentation broth either during or after the fermentation has been completed, recovering the product of interest from the fermentation broth, and optionally subjecting the recovered product to further purification. This method is further illustrated in the examples below.

In a still further alternative aspect the invention relates to a method of preparing a product essentially free from TPAP activity, wherein the protein product of interest is encoded by a DNA sequence present in a TPAP expressing cell. The method comprises cultivating the TPAP expressing cell encoding the product under conditions permitting the expression of the product, subjecting the resultant culture broth to a combined pH and temperature treatment so as to reduce the TPAP activity substantially, and recovering the product from the culture broth. Alternatively, the combined pH and temperature treatment may be performed on an enzyme preparation recovered from the culture broth. The combined pH and temperature treatment may optionally be used in combination with a treatment with a TPAP inhibitor.

In accordance with this aspect of the invention it is possible to remove at least 60% of the TPAP activity, preferably at least 75% of the activity, more preferably at least 85% of the activity, still more preferably at least 95% of the activity, and most preferably at least 99% of the TPAP activity. It is contemplated that a complete removal of TPAP activity may be obtained by use of this method.

The combined pH and temperature treatment is preferably carried out at a pH in the range of 6.5–7 and a temperature in the range of 25°–40° C. for a sufficient period of time for obtaining the desired effect. Typically, 0.5–1 hour is sufficient for obtaining the desired effect.

The methods used for cultivation and purification of the product of interest may be performed by methods known in the art, e.g. as described herein above.

The methods of the invention for producing an essentially TPAP-free product is of particular interest in the production of eukaryotic proteins, in particular fungal proteins such as enzymes. The enzyme product may be selected from, e.g., an amylolytic enzyme, a lipolytic enzyme, a proteolytic enzyme, a cellulytic enzyme, an oxidoreductase or a plant cell-wall degrading enzyme. Examples of such enzymes include AMG, amylase, lipase, cutinase, esterase, cellulase, hemicellulase, protease, peroxidase, laccase, phenoloxidase, catalase, glucose oxidase, phytase, lyase, pectinase, glucosidase, mannosidase, isomerase, invertase, trasferase, ribonuclease, galactosidase, transglutaminase and chitinase. The TPAP-deficient cells may also be used to express heterologous proteins of pharmaceutical interest such as hormones, growth factors, receptors, and the like.

It will be understood that the term "eukaryotic proteins" is intended to include not only native proteins, but also those proteins, e.g. enzymes, which have been modified by amino acid substitutions, deletions or additions, or other such modifications to enhance activity, thermostability, pH tolerance and the like.

In a further aspect the invention relates to a protein product essentially free from TPAP activity which is produced by the method of the invention. In a preferred embodiment the protein product is amyloglucosidase.

A final aspect of the invention relates to the strains DSM 11128 and DSM 11129, or a mutant thereof comprising an analogue of the DNA sequence shown in SEQ ID No. 16. DSM 11128 and DSM 11129 are described in further detail below in Example 10.

EXAMPLE 1

Purification and Characterization of *A. niger* TPAP and AMG

Materials and Methods

TPAP substrate: Phe-Pro-Ala-pNA

Protease inhibitors: Ala-Ala-Phe-chloromethylketone
  Benzyloxycarbonyl-Ala-Pro-Phe-chloromethylketone
  Benzyloxycarbonyl-Gly-Gly-Phe-chloromethyl-ketone
(substrate and all inhibitors from Bachem, Switzerland)

Purification of TPAP

TPAP was purified from a commercial *A. niger* AMG preparation (Novo Nordisk A/S, Denmark). A sample of 300 ml of formulated AMG was repeatedly diluted and concentrated at 4° C. in a Filtron® concentrator (Filtron) equipped with a 3 kDa cutoff membrane until the conductivity was less than 1.5 mS/cm. All other purification steps were carried out at ambient temperature.

Cation exchange chromatography employing a NaCl gradient

The concentrate (600 ml) was adjusted to pH 4.0 and filtered before application to a 200 ml S-Sepharose (Pharmacia) column equilibrated with 20 mM sodium acetate, pH 4.0. A flow rate of 10 ml/min was used. The TPAP was eluted using a linear NaCl gradient of 0 to 0.2M, in 10 column volumes. One pool was made from the eluted peptidase activity. A buffer change to 20 mM sodium acetate, pH 5.5, was made in an Amicon cell (Amersham) equipped with a Diaflo membrane (Amersham) with a molecular weight cutoff of 10 kDa.

Anion exchange chromatography

The pool from the S-Sepharose column was further purified on a 50 ml HiLoad Q-Sepharose HP (Pharmacia) column equilibrated with 20 mM sodium acetate, pH 5.5. Elution of TPAP was performed using a linear NaCl gradient of 0 to 0.5M in 15 column volumes. The protein was applied to the column at a flow rate of 8.0 ml/min and eluted at 5.0 ml/min. Fractions containing TPAP activity were pooled and dialyzed against 20 mM sodium acetate, pH 4.0, in an Amicon cell as described above.

Cation exchange chromatography employing a pH gradient

The pool from the HiLoad Q-Sepharose HP column was further purified on a Mono S column (5/5)(Pharmacia) equilibrated with 20 mM sodium acetate, pH 4.0. A gradient from pH 4.0 to pH 6.0 was made in 30 column volumes using 20 mM sodium acetate, pH 4.0 and 20 mM sodium acetate, pH 6.0. The flow rate was 1.0 ml/min. Two isoenzymes of TPAP, named TPAP-I and TPAP-II, eluted at pH 5.1 and 5.2, respectively.

Purification of AMG G1 and $AMG_{trunc}$

The G1 form of AMG was purified from a commercial AMG preparation (Novo Nordisk A/S, Denmark) by anion exchange chromatography using Q-Sepharose (Pharmacia). A 50 ml column was equilibrated with 20 mM sodium acetate, pH 5.5 and the G1 form eluted using a linear NaCl gradient of 0 to 0.6M NaCl in 8 column volumes. The flow rate was 8.0 ml/min.

A fraction termed $AMG_{trunc}$ was purified after TPAP treatment of AMG G1 on a Mono Q column equilibrated with 20 mM sodium acetate, pH 4.3. A linear NaCl gradient from 0 to 1.0M in 30 column volumes was used for elution. The flow rate was 1.0 ml/min.

Destabilization assay

Aliquots of purified AMG G1 were incubated with different mixtures of TPAP in 0.1M sodium acetate, pH 4.3 for several weeks at 37° C. The final volume was either 1 or 2 ml with a concentration of AMG G1 of 10 AGU/ml. One hundred $\mu$l of the incubation mixture were withdrawn and diluted to 2 AGU/ml with 0.1M sodium acetate, pH 4.3. A heat treatment at 65° C. for 30 min was carried out on aliquots of the diluted sample. After cooling the samples to ambient temperature, the activities of untreated and heat treated samples were measured in microtiter plates using the chromogenic substrate p-nitrophenyl-α-D-glycopyranoside (pNPG) (Merck, Art. 6792). Fifty $\mu$l of 3 mM pNPG in 0.1M sodium acetate, pH 4.3, was added to a 25 $\mu$l sample which was then incubated for 30 min at ambient temperature. The reaction was stopped by addition of 75 $\mu$l of 0.1M sodium tetraborate. The absorbance at 405 nm was measured in a UV-max kinetic microplate reader (Molecular Devices). The $T_{30}$ was calculated as the percentage of activity retained after heat treatment. All measurements were made in duplicate.

TPAP assay

The assay was performed either in a microtiter plate reader or in a spectrophotometer using a substrate concentration of 0.2 mM Phe-Pro-Ala-pNA in 0.1M sodium acetate buffer, pH 4.3. A 5 mM stock solution of Phe-Pro-Ala-pNA was made in DMSO and diluted before use. The reaction was followed for 4 min at 405 nm, either in a UV-max kinetic microplate reader or a spectrophotometer, and the initial rate of cleavage calculated.

Inhibition of TPAP

Aliquots containing 4 $\mu$g TPAP were incubated with one of the following protease inhibitors: 1 mM Ala-Ala-Phe-chloro-methylketone, 1 mM benzyloxycarbonyl-Ala-Pro-Phe-chloromethyl-ketone and 1 mM benzyloxycarbonyl-Gly-Gly-Phe-chloromethylke-tone. Following a 30 min incubation the residual activity was determined.

Storage stability of filtrated fermentation broths

The culture broths were centrifuged and sterile filtered through a 0.22 $\mu$m filter. Potassium sorbate and sodium benzoate were added to the broths for a final concentration of 0.1% (weight/volume) each, and the pH was adjusted to 4.3. Either 200 $\mu$l of 10 mM Ala-Ala-Phe-chloromethylketone or 200 $\mu$l of 0.1M sodium acetate, pH 4.3 were added to 2 ml aliquots. Samples were withdrawn and diluted to 2 AGU/ml before the $T_{30}$ determination as described above.

Determination of AMG activity (AGU)

AMG activity was determined as described By K. A. Holm (1980, Anal. Chem. Acta. 117:359–362). In brief, the method is based on the hydrolysis of maltose by AMG to form alpha-D-glucose. After a short continuous dialysis, the concentration of glucose is determined by a glucose dehydrogenase (GlucDH) reaction performed at pH 7.6. Standard conditions for the automated Auto-Analyzer method are:

Substrate: maltose 28 mM

Incubation buffer: acetate 0.1M, pH 4.3

Incubation temperature: 37° C.

Incubation time: 5 min.

The enzyme activity range of the method is 0.5–4 AGU/ml.

Results

TPAP was purified to homogeneity from a commercial AMG preparation (Novo Nordisk A/S, Denmark) according to the purification scheme shown in Table 1. The elution profile from the final cation exchange column revealed the presence of two isoenzymes of TPAP, TPAP-I and TPAP-II, with a pI 5.1 and 5.2, respectively. Both isoforms were pure as judged by SDS-PAGE and N-terminal sequencing, but the specific activities of the enzymes differed (cf. Table 1). The specific activity of TPAP-II was 20% higher than TPAP-I.

A deamidation of one or several asparagine or glutamine residues, either in the fermentation broth or during purification, can explain the small difference in pI between the two isoforms of TPAP.

EXAMPLE 2

Peptide sequences of *A. niger* TPAP

N-terminal amino acid sequencing of intact *A. niger* TPAP-I and TPAP-II (Example 1) as well as of peptides derived from TPAP-I was performed in an Applied Biosystems 473A sequencer (Applied Biosystems, Foster City, Calif.) operated according to the manufacturer's instructions.

The N-terminal amino acid sequences of intact TPAP-I and TPAP-II were determined for 30 residues. The two sequences were identical and found to be: Ala-Gln-Asn-Thr-Ser-His-Cys-Asp-Ser-Ile-Ile-Thr-Pro-His-Cys-Leu-Lys-Gln-Leu-Tyr-Asn-Ile-Gly-Asp-Tyr-Gln-Ala-Asp-Pro-Lys (SEQ ID No. 4). The sequence did not show any homology to other proteins.

Following denaturation, reduction and S-carboxymethylation, peptides were derived from TPAP-I by proteolytic cleavage using the lysyl-specific protease from *Achromobacter lyticus*. The resultant peptides were fractionated and purified using reverse phase HPLC. The purity and mass of the peptides were evaluated using matrix assisted laser desorption ionization time-of-flight mass spectrometry in a VG Analytical TofSpec (VG Analytical, Manchester, UK) operated according to the manufacturer's recommendations. The following 7 peptides were sequenced:

TABLE 1

Purification of TPAP from a commercial AMG preparation

| Pools | | Volume ml | Total protein mg[#] | Total activity μmol/min | Specific activity μmol/min/mg[#] | Yield % | Purification fold |
|---|---|---|---|---|---|---|---|
| UF-concentrate | | 600 | 117,000 | 1,900 | 0.016 | 100 | — |
| S-sepharose | | 1250 | 410 | 1,100 | 2.7 | 58 | 1170 |
| HPQ-sepharose | | 45 | 27 | 390 | 14 | 20 | 880 |
| Mono S | TPAP-I | 8.5 | 6.0 | 132 | 22 | 7 | 1380 |
| | TPAP-II | 8 | 4.9 | 132 | 27 | 7 | 1680 |

[#]based on the assumption that 1 mg/ml gives $A_{280}$ = 1
*measured as release of pNA in the TPAP assay pH optimum The pH optimum of TPAP was determined using the same procedure as in the TPAP assay described above. One hundred mM acetate buffer was used to regulate the pH. The resulting pH optimum curve is shown in FIG. 1. It is seen that the TPAP activity is optimal at a pH in the range of 5.0–5.5, but in particular, at pH 5.25.

Determination of temperature optimum for TPAP

The temperature/activity relationship of TPAP was determined in 0.1M sodium acetate buffer, pH 5.5, using the TPAP assay described above. As can be seen from Table 2, TPAP has maximal activity in the temperature range 45°–55° C.

TABLE 2

Effect of temperature on TPAP activity

| Temperature (°C.) | 25 | 30 | 35 | 40 | 45 | 50 | 55 | 60 | 65 |
|---|---|---|---|---|---|---|---|---|---|
| Rel. act. (%) | 42 | 52 | 63 | 78 | 100 | 99 | 98 | 51 | 8 |

Mass spectrometry

Matrix assisted laser desorption ionization time-of-flight mass spectrometry of TPAP purified from *A. niger* gave a broad signal indicating that the TPAP is glycosylated. The average mass was found to be 54.5 kDa.

Peptide 1
Ala-Gln-Asn-Thr-Ser-His-Cys-Asp-Ser-Ile-Ile-Thr-Pro-His-Cys-Leu-Lys

Asn3 is glycosylated as shown by mass spectrometry and amino acid sequencing. Peptide 1 is identical to amino acid residues 1-17 of intact TPAP and thus of the sequence shown in SEQ ID No. 4.

Peptide 2
Gln-Leu-Tyr-Asn-Ile-Gly-Asp-Tyr-Gln-Ala-Asp-Pro-Lys

Peptide 2 is identical to amino acid residues 18-30 of intact TPAP (and thus of the amino acid sequence shown in SEQ ID No. 4). Peptide 2 was recovered in two forms as revealed by mass spectrometry and amino acid sequencing. In one form Gln is the N-terminal residue and in the other, the N-terminal Gln has been converted to a pyroglutamate residue.

Peptide 3
Thr-Ser-Pro-Glu-Gln-Ala-Val-Ser-Phe-Ser-Ser-Gly-Gly-Phe-Ser-Asp-Leu-Trp-Pro-Arg-Pro-Ser-Tyr-Gln-His (SEQ ID No. 5)

Peptide 4
Phe-Ser-Gly-Leu-Phe-Asn-Ala-Ser-Gly-Arg-Ala-Phe-Pro-Asp-Val-Ser-Ala-Gln-Gly-Val-Asn-Tyr-Ala-Val-Tyr-Asp-Lys (SEQ ID No. 6)

Asn6 is glycosylated as shown by mass spectrometry and amino acid sequencing.

Peptide 5
Ile-Gly-Phe-Ala-Ser-Tyr-Leu-Gln-Glu-Tyr-Ala-Arg-Tyr-Ala-Asx-Leu-Glu-Arg-Phe-Glu-Gln-His-Leu (SEQ ID No. 7)

It was not possible to discriminate whether Asx15 is an Asp or Asn residue.

Peptide 6
Xaa-Leu-Asx-Leu-Gln-Tyr-Ile-Leu-Gly-Val-Ser-Ala-Pro-Val-Pro-Ile-Thr-Glu-Tyr-Ser-Thr-Gly-Gly-Arg-Gly-Glu-Leu-Val-Pro- (SEQ ID No. 8)

It was not possible to discriminate whether Asx3 is an Asp or Asn residue. Xaa1 designates an unidentified residue.

Peptide 7
Gly-Ala-Leu-Asx-Asp-Ile-Val-Asn-Gly-Thr-Ser-Val-Gly-Gln-Asp-Gly-Arg-Asn-Arg-Phe-Gly-Gly-Thr-Pro-Asn-Gly-Ser- (SEQ ID No. 9)

It was not possible to discriminate whether Asx4 is an Asp or Asn residue. Note that Asn25 is not glycosylated although it is found in the concensus sequence for N-glycosylation.

Peptide sequences of *A. oryzae* TPAP

N-terminal amino acid sequencing of intact TPAP as well as of peptides derived from TPAP was carried out in an Applied Biosystems 473A protein sequencer according to the manufacturer's instructions.

The N-terminal amino acid sequence of intact TPAP were determined following SDS-PAGE and electroblotting onto a PVDF-membrane using standard procedures. The following 23 residue amino acid sequence was identified:
Ala-Lys-Xaa-Ile-Ser-His-Yaa-Asp-Ser-Ile-Ile-Thr-Pro-Pro-Yaa-Leu-Lys-Glu-Leu-Tyr-Asn-Ile-Gly (SEQ ID No. 14)

This sequence is clearly homologous to the N-terminal amino acid sequence of TPAP from *A. niger*. Based on this homology Xaa is most likely to be a glycosylated Asn residue while Yaa probably represents a Cys residue.

Following denaturation, reduction and S-carboxymethylation, peptides were derived from TPAP by proteolytic cleavage using the lysyl-specific protease from *Achromobacter lyticus*. The resultant peptides were fractionated and purified using reverse phase HPLC. The purity and mass of the peptides were evaluated using matrix assisted laser desorption ionization time-of-flight mass spectrometry using a VG Analytical TofSpec (VG Analytical, Manchester, UK) operated according to the manufacturer's recommendations. The following 4 peptides were sequenced:

Peptide 8
Glu-Leu-Tyr-Asn-Ile-Gly-Asp-Tyr-Gln-Ala-Asp-Ala-Asn-Ser-Gly-Ser-Lys (SEQ ID No. 10)

This peptide overlaps with the 6 last amino acid residues determined by the N-terminal sequencing of intact TPAP thereby extending the N-terminal sequence to 34 residues.

Peptide 9
Thr-Thr-Pro-Glu-Arg-Gly-Thr-Tyr-Phe-Ser-Ser-Gly-Gly-Phe-Ser-Asn-Tyr-Trp-Pro-Arg-Pro-Glu-Trp-Gln-Asn-Gln-Ala-Val-Ala-Ser-Tyr-Leu (SEQ ID No. 11)

This peptide is homologous to peptide 3 from *A. niger* TPAP.

Peptide 10
Gly-Thr-Leu-Gly-Glu-Phe-Asp-Gly-Thr-Ser-Ala-Ser-Ala-Pro-Ala-Phe-Ser-Ala-Val-Ile-Ala-Leu-Leu-Asn-Asp-Ala-Arg-Leu-Arg-Ala-Gly-Lys-Pro-Thr-Leu-Gly-Phe-Leu-Asn-Pro-Trp-Leu-Tyr-Lys (SEQ ID No. 12)

Peptide 11
Thr-Gly-Arg-Gln-Gly-Leu-Gln-Asn-Ile-Thr-Leu-Gly-Ala-Ser-Ile-Gly-Xaa-Thr-Gly-Arg-Ala-Arg-Phe-Gly-Gly-Ala-Pro-Asn-Gly-Gly-Pro-Val-Val-Pro-Tyr-Ala-Ser (SEQ ID No. 13), Xaa17 designates an unidentified residue.

EXAMPLE 3

Amino Acid Composition of *A. niger* TPAP-I and TPAP-II

The amino acid compositions of *A. niger* TPAP-I and TPAP-II were determined. Duplicates of lyophilyzed aliquots of TPAP-I and TPAP-II were hydrolyzed in 6N HCl containing 0.1% phenol at 110° C. in vacuo for 16 h. Tryptophan was determined following hydrolysis in 3M methanesulfonic acid. All other amino acids were determined using an Applied Biosystems 420A amino acid analysis system operated according to the manufacturer's instructions. The results show that within experimental error TPAP forms I and II have identical amino acid compositions as shown in Table 3 below.

TABLE 3

| Amino acid composition of *A. niger* TPAP-I and TPAP-II | | |
|---|---|---|
| | TPAP I (Mol %) | TPAP II (Mol %) |
| Asx | 13.1 | 13.4 |
| Glx | 8.2 | 7.9 |
| Ser | 10.5 | 10.7 |
| Gly | 13.7 | 13.1 |
| His | 0.5 | 0.5 |
| Arg | 3.1 | 3.1 |
| Thr | 5.7 | 5.6 |
| Ala | 8.0 | 7.9 |
| Pro | 7.2 | 7.3 |
| Tyr | 3.7 | 3.8 |
| Val | 6.0 | 5.9 |
| Met | 0.3 | 0.5 |
| Cys | 0.6 | 0.7 |
| Ile | 2.5 | 2.5 |
| Leu | 8.4 | 8.4 |
| Phe | 4.5 | 4.8 |
| Lys | 3.1 | 3.0 |
| Trp | 0.9 | 1.0 |

EXAMPLE 4

Determination of Monosaccharide Composition of *A. niger* TPAP

Duplicates of lyophilyzed aliquots of TPAP-I and TPAP-II were hydrolyzed in 2M TFA (trifluoroacetic acid) at 100° C. in vacuo for 1 h, 2 h and 4 h. Following hydrolysis the monosaccharide compositions were analyzed by high performance ion exchange chromatography using a Carbo-Pac™ PA1 column (Dionex, Sunnyvale, Calif.) eluted with 16 mM NaOH. The monosaccharides were detected by pulsed amperometric detection. Due to differences in the stability of the monosaccharides in 2M TFA, the amount of galactose was determined after 1 h of hydrolysis, the amount of mannose after 2 h and the amount of glucosamine after 4 h of hydrolysis. The results obtained indicate very minor differences in mannose content of TPAP-I and TPAP-II as shown in the table below.

TABLE 4

| Monosaccharide compositions of TPAP-I and TPAP-II. | | |
|---|---|---|
| | TPAP-I (pmol/pmol) | TPAP-II (pmol/pmol) |
| Glucosamine | 4 | 4 |
| Galactose | 12 | 11 |
| Mannose | 52 | 47 |

The results are given in pmol monosaccharide/pmol protein as determined from amino acid analysis.

EXAMPLE 5

AMG Cleavage by *A. niger* TPAP

The ability of *A. niger* TPAP to destabilize the AMG G1 form was investigated using purified AMG and TPAP, obtained as described in the Materials and Methods section in Example 1, at TPAP/AMG ratios equal to those in formulated products for commercial use. Amino acid sequencing of the destabilized preparations revealed a modification in the N-terminal of the catalytic domain of AMG. A tripeptide comprising the first three amino acid residues (Ala-Thr-Leu) had been cleaved off by the peptidase suggesting that the enzyme responsible is a tripeptidyl aminopeptidase. The classification as a tripeptidyl aminopeptidase is based on the cleavage of AMG as well as of the chromogenic substrate Phe-Pro-Ala-pNA. This was further supported by its failure to cleave another chromogenic tripeptidyl substrate, Succinyl-Ala-Ala-Ala-pNA, wherein the free amino group at the N-terminus has been succinylated, thereby rendering the substrate inaccessible to cleavage by TPAP. The TPAP cleavage of the AMG batches was not complete after 3 weeks storage, as a mixture of intact and truncated AMG ($AMG_{trunc}$) was detected by amino acid sequencing.

The effect of dose and temperature on the destabilization of AMG by TPAP was investigated using purified enzymes and applying TPAP/AMG ratios similar to the ratios measured in several fermentations. The TPAP activity was most pronounced at 37° C., but destabilization of AMG was also observed at 25° C. after 27 days of storage. The stability of AMG was not affected following storage at 4° C., indicating that TPAP has very low activity at 4° C.

EXAMPLE 6

Substrate Specificity of *A. niger* TPAP

Using various native protein and peptide substrates TPAP was found to be highly non-specific with respect to the amino acid residue at the N-terminal of the cleavage point, including proline and carboxylmethylated cysteine. However, a Pro residue C-terminal to the cleavage point completely inhibits cleavage by TPAP. Specific cleavage products obtained by subjecting native proteins to TPAP treatment include the tripeptide sequences IPE, YVD, WRQ, KGA, LPS, ANL, NGT, LMQ, YFE, GPG, GGG, ADG, RST, SVE, KKP, EGV, NTG, AGD, RHN, LKT, VEK, KPE, GVN, TGA, GDR, HNL, HSQ, GTF, TSD, YSK, YLD, SRR, AQD, FVQ, WLM and ATL.

EXAMPLE 7

Inhibition of *A. niger* TPAP Activity

The protease inhibitor, cloromethyl-ketone Ala-Ala-Phe-CMK (AAF-CMK), was found to completely inhibit TPAP when tested under the conditions described above.

When added to fermentation broths, AAF-CMK can totally inhibit the TPAP activity. The thermostability of five different AMG batches stored for two weeks at 37° C. in the presence of active TPAP were notably destabilized, whereas the thermostability of all 5 AMG batches remained unchanged when TPAP had been inhibited.

EXAMPLE 8

Inactivation of TPAP

Aliquots of 10 ml culture broths obtained from a cultivation of an AMG producing *A. niger* strain were adjusted to either pH 6.5 or pH 7.0 with NaOH. The samples were incubated at 25° C., 40° C. or 50° C. for one hour, then the pH was adjusted to 4.3 with a acid, and the stability of the treated samples was measured after a period of storage. As shown below in Table 5, this simple procedure resulted in an efficient removal of TPAP activity. For example, a heat treatment of 40° C. for one hour of an aliquot of culture broth at pH 6.5 reduced the TPAP activity to 5% and did not significantly reduce the thermostability of AMG after two weeks of storage at 40° C.

TABLE 5

Effect of pH and temperature on stability

| pH/temp. 1 hour | TPAP after treatment | AMG after treatment | T30 initial | T36 2 weeks | TPAP 2 weeks |
|---|---|---|---|---|---|
| Reference | 100% | 100% | 50% | 31% | 80% |
| 6.5/25° C. | 90 | 100 | 46 | 43 | 42 |
| 6.5/40° C. | 5 | 97 | 47 | 53 | |
| 6.5/50° C. | <1 | 90 | — | — | |
| 7.0/25° C. | 86 | 99 | 48 | 44 | |
| 7.0/40° C. | <1 | 92 | 48 | 55 | |
| 7.0/50° C. | <1 | 85 | — | — | |

All values for TPAP and AMG are indicated as a percentage relative to the activity at the reference time point.

EXAMPLE 9

PCR Cloning

From the N-terminal amino acid sequence of *A. niger* TPAP shown in SEQ ID No. 3, four PCR primers in Table 6 were designed. Genomic DNA from a strain of *A. niger* was used as the template in four PCR reactions. PCR products of the expected size 65 bp were purified and cloned into the plasmid pCR™II (Invitro BV, 9351 NV Leek, NL). Sequencing of the insert for two of three clones revealed the presence of degenerate sequences corresponding to the primers and flanking a sequence identical to the N-terminal amino acid sequence of *A. niger* TPAP.

In order to clone a larger DNA fragment encoding the tripeptidyl aminopeptidase, the primer #6010 (GCACTGTCTGAAGCAGCTGTACAACATCGGTG) was designed to correspond to the invariant N-terminal sequence. Three PCR primers in Table 6 (#5988, #5989 and #5990) were designed from two other peptide sequences (see Example 3) and individually paired with primer #6010 in separate PCR reactions using genomic *A. niger* DNA as the template. The reactions were done at two annealing temperatures, 42° C. and 45° C. Reaction #6010/#5989 produced one fragment of approximately 80 bp whereas reaction #6010/#5990 yielded three fragments of approximately 120 bp, 500 bp, and 950 bp at both temperatures. Reaction #6010/#5988 produced a fragment of approximately 120 bp at 42° C., but at 45° C. a fragment of approximately 950 bp was seen. Because the 950 bp fragment contained the sequence of interest, it was inserted into the pCR II AT vector.

TABLE 7

Oligonucleotide Primers

5765
5'- G A C T C C A T C A T C A C C C C
         T   T     T     T     T
             A     A     A     A
             G                 G

5766
5'- G A C A G C A T C A T C A C C C C
         T     T     T     T     T
                                 A
                                 G

5767
    C T G A T G G T T C G G C T G G G -5'
        A     A     C     A     A

5768
    C T G A T G G T T C G C C T G G G -5'
        A     A     C     T     A

5988
    A T A C G A C A A A T A C T A T T -5'
        G     C     C     G     G
              G     G
              T     T

5989
    A T A A A A C T C C T C A T A C G -5'
        G G   C     T     T     G
              G

5990
    C T T C T A A A C T T G T T G T -5'
        C     G     G     C     C

The 950 bp fragment was sequenced from both ends. This fragment was found to encode the N-terminal sequence of TPAP. The partial sequence of the N-terminal region is shown in SEQ ID No. 2; the partial sequence obtained from sequencing at the C-terminal is shown in SEQ ID No. 3. The sequence of the entire approximate 950 base pair size fragment was determined to be 908 bp in size, and is shown in SEQ ID No. 1.

An E. coli strain harboring the 908 kb fragment was deposited with the Deutsche Sammlung von Microorganismen und Zellkulturen GmbH, Mascheroder Weg 1b, D-38124 Braunschweig, Germany on Dec. 5, 1994, as DSM 9570, under the provisions of the Budapest Treaty.

Southern analysis

Genomic DNA from a strain of A. niger and from A. oryzae strain IFO 4177 was isolated as described previously (Yelton et al., 1984, Proc. Natl. Acad. Sci. USA. 81:1470–1474). Genomic DNA was digested with appropriate restriction enzymes, fractionated on a 0.7% agarose gel, and blotted to Immobilon™-N as described by the manufacturer (Millipore Corp, Bedford Mass.; USA). The membranes were probed for the presence of the $\alpha$-$^{32}$P dATP labelled 950 bp TPAP gene sequence (Dupont NEN Research Boston Mass., USA) by random priming according to the method described by Feinberg et al. (1983, Anal. Biochem. 132:6). The membranes were then incubated for 2 hours at 65° C. in hybridization solution (5×SSC (0.15M NaCl, 0.015M trisodium citrate), 10×Denhardt (0.2% Ficoll, 0.2% polyvinyl pyrrolidone, 0.2% bovine serum albumin), 10 mM EDTA, 1% SDS, 150 μg/ml poly A, 50 μg/ml yeast tRNA). Next, the radioactively labelled probe was added and incubated at 65° C. overnight with gentle agitation. The membranes were washed twice at 30° C. for 15 minutes in 2×SSC, 1% SDS. Finally, the membranes were dried, covered with plastic wrap, and exposed to X-ray film (Fuli-RX, FUJI Photo Film Co. LTD) at −70° C.

The results show that both strains each contain the same gene sequence encoding the TPAP.

EXAMPLE 10

Cloning of the A. niger TPAP

Genomic DNA from a strain of A. niger was isolated as described previously (Yelton et al., 1984, Proc. Natl. Acad. Sci. USA. 81:1470–1474). Genomic DNA was partially digested with the restriction enzyme Tsp 509I, and fragments between 2–6 kb were purified, then cloned into the system λZipLox, EcoRI arms as described by the manufacturer (GIBCO BRL, Life Technologies, Inc, Bethesda Md., USA).

The genomic library was screened by excision of the genomic clones in pZL1 from λZipLox phage as described by the manufacture. Ten plates was made containing an estimated 1000 colonies per plate. The plates were incubated at 37° C. overnight. Sterilized Whatman 540 filters were placed upon the colonies which were incubated for two more hours at 37° C. The filters were transferred to LB plates containing chloramphenicol at 200 μg/ml and the plates were incubated overnight at 37° C. The next day the filters were washed twice in 0.5M NaOH for 5 minutes, followed by two washes in 0.5M Tris-HCl pH7.4 for 5 minutes, and then twice in 2×SSC for 5 minutes. The washed filters were wet down with ethanol and allowed to air dry.

The filters were incubated in a solution containing an $\alpha$-$^{32}$P labelled 0.9 kb DNA fragment made from the TPAP sequence in DSM 9570. The hybridization was carried out for 16 hours at 65° C. in 10×Denhardt, 5×SSC, 20 mM EDTA, 1% SDS, 150 μg/ml poly A and 50 μg/ml yeast tRNA. After hybridization the filters were washed in 2×SSC, 0.1% SDS at 65° C. twice and exposed to X-ray films. One colony showed hybridization to the probe, and is from hereafter called pJaL406.

Further analysis by restriction digest and sequencing of this clone indicated that the C-terminal region of the TPAP gene was missing. Therefore, a genomic Southern was made. Genomic DNA from A. niger was digested with appropriate restriction enzymes, fractionated on a 0.7% agarose gel, and blotted to Immobilon™-N as described by the manufacturer. The membranes were probed for the presence of a 900 bp SpeI fragment from pJaL406 which had been labelled with $\alpha^{32}P$ dATP (NewEngland) by random priming (Feinberg et al., 1983, Anal. Biochem. 132:6). The membranes were then incubated for 2 hours at 65° C. in hybridization solution (5×SSC, 10×Denhardt, 10 mM EDTA, 1% SDS, 150 µg/ml poly A RNA, 50 µg/ml yeast tRNA). The radioactive labelled probe was then added and incubated at 65° C. overnight with gentle agitation. The membrane was washed twice at 65° C. for 15 minutes in 2×SSC, 1% SDS. The membrane was then dried and exposed to X-ray film as described above. The results show that the probe hybridized to a 2.4 kb HindIII/BglII fragment.

Genomic DNA was digested with HindIII and BglII, fractionated on a 0.7% agarose gel, and fragments in the size of 2.0–2.5 kb were purified, and cloned into the corresponding sites in the vector pIC19R. An estimated 2000 colonies were screened with the above probe as described above. Four positive colonies were obtained, and sequencing confirmed that they contained the C-terminal half of the TPAP gene. One of these clones was named pJaL435. The nucleotide sequence of the protein coding part and the flanking regions is shown in SEQ ID No. 16. The amino acid sequence of the protein is shown in SEQ ID No. 17. The nucleotide sequence showed that the TPAP gene has an open reading frame coding for 611 amino acids and is interrupted two introns of 67 bp and 71 bp, respectively. The start codon is followed by a sequence coding for a putative signal peptide of 25 amino acids.

An *E. coli* strain harboring pJaL406 and one harboring pJaL435 were deposited with the Deutsche Sammlung von Microorganismen und Zellkulturen GmbH, Mascheroder Weg 1b, D-38124 Braunschweig, Germany on 2 Sep. 1996, as DSM 11128 and DSM 11129, respectively, under the provisions of the Budapest Treaty.

Thus, the complete DNA sequence encoding the TPAP from *A. niger* can be obtained by combining the N-terminal sequence of the *A. niger* TPAP present in DSM 11128 with the C-terminal sequence of the *A. niger* TPAP present in DSM 11129.

EXAMPLE 11
Purification and Characterization of *A. oryzae* TPAP
Materials & Methods The starting material for the purification was the supernatant of an *A. oryzae* IFO 4177 culture fermented at pH 5 in a soy containing medium. After fermentation, the culture broth was centrifuged to remove the bulk of the cellular material.
Purification Approx. 4 L of supernatant was sterile filtered on a Seitz EKS plate (Seitz). The EKS filtrate was ultrafiltrated on a 3 kDa cut-off Filtron cassette (Minisette, Filtron) to a minimal volume of 240 ml. One hundred seventy ml of the ultrafiltrate was precipitated with solid ammonium sulphate (AMS) to give an AMS saturation of approximately 90%. After stirring for at least 30 min., the AMS precipitate was recovered by centrifugation in a Sorvall RC3B centrifuge (4500 rpm, 15 min., room temp). One hundred ml of deionized water was added to the AMS precipitate to dissolve the protein and 1% (w/v) FGV120 activated charcoal was added to remove colour. After stirring for approximately 1 hour, the suspension was filtered on a Seitz EK1 plate (Seitz) to remove the charcoal. The EK1-filtrate was dialyzed against a buffer of 100 mM $H_3BO_3$, 10 mM dimethyl glutaric acid, 2 mM $CaCl_2$, pH 5, followed by dialysis in deionized water. After second EK1-filtration the 260 ml of dialysate was recovered and frozen in aliquots.

One 120 ml aliquot of the dialysate was thawed and applied to a 1.4 L G25 Sephadex column equilibrated in 20 mM sodium acetate, pH 5.0. To remove colour and very acidic proteins, the G25-filtrate (flow-through) was applied to a 40 ml Q-sepharose FF column equilibrated in the same buffer (20 mM sodium acetate, pH 5.0). After washing the column, bound protein was eluted with a linear NaCl gradient, 0 to 200 mM. Fractions from the column were analyzed for TPAP activity. Seventy percent of the TPAP activity was seen in the run-through, whereas most of the protein was bound to the column.

The run-through from the Q-sepharose column was applied to a 50 ml S-sepharose HP column equilibrated in 20 mM sodium acetate, pH 5.0. After washing the column, bound protein was eluted with a linear NaCl gradient, 0 to 200 mM. Fractions from the column were analyzed for TPAP activity. Most of the TPAP activity (75%) was again seen in the run-through. The rest of the TPAP activity was in the start of the NaCl gradient. The run-through and the first 11 fractions were pooled and dialyzed against a buffer of 50 mM $H_3BO_3$, 5 mM dimethyl glutaric acid, 1 mM $CaCl_2$, pH 6.0.

After adjusting the pH of the dialyzed pool to pH 7.0, the dialysate was applied to a 23 ml SOURCE Q column (Pharmacia) equilibrated in 50 mM $H_3BO_3$, 5 mM dimethyl glutaric acid, 1 mM $CaCl_2$, pH 7.0. After washing the column, bound protein was eluted with a linear NaCl gradient of 0 to 500 mM. Fractions from the column were analyzed for TPAP activity. Ninety-five percent of the TPAP activity was seen in the run-through.

The run-through was dialyzed against 20 mM sodium acetate, pH 4.0, then applied to a 50 ml S-sepharose HP column equilibrated in the same buffer. After washing the column, bound protein was eluted with a NaCl gradient, 0 to 200 mM. Analysis of fractions collected from the column indicated that the TPAP activity was eluted with 100 mM NaCl. The fractions containing TPAP activity were pooled and dialyzed against 20 mM sodium acetate, pH 4.0. To further improve upon the purification achieved by the S-sepharose column, the dialyzed pool was applied to an 8 ml SOURCE S column equilibrated in the same buffer of 20 mM sodium acetate, pH 4.0. After washing the column, bound protein was eluted with a NaCl gradient, 0 to 200 mM. TPAP activity was found in fractions from the column eluted with 60 mM NaCl.

The TPAP activity was pooled and dialyzed against 20 mM sodium acetate, pH 5.5, then applied to a 23 ml SOURCE Q column equilibrated in 20 mM sodium acetate, pH 5.5. After washing the column, bound protein was eluted with a NaCl gradient, 0 to 200 mM. Fractions from the column were analyzed by SDS-PAGE and for TPAP activity. The TPAP activity was eluted with 30 mM NaCl. SDS-PAGE analysis revealed a major band at 30 kDa which co-purified with the 65 kDa TPAP band. The TPAP band was diffuse whereas the 30 kDa band was sharp, indicating that TPAP is glycosylated whereas the 30 kDa band is not.

The TPAP containing fractions were pooled and concentrated to 1 ml by ultrafiltration and applied to a 150 ml Sephacryl S-100 column equilibrated in a buffer of 20 mM Tris-acetate, 100 mM NaCl, pH 5.5 using a 1.0 ml/min flow rate to separate the two bands. The TPAP activity containing fractions were pooled as *A. oryzae* TPAP.
Mass spectrometry Matrix assisted laser desorption ionization time-of-flight mass spectrometry of TPAP purified from *A. oryzae* gave a broad signal indicating that the TPAP is glycosylated. The average mass was found to be 55.0 kDa.

pH profile of A. oryzae TPAP

The pH dependency of the activity of TPAP from A. oryzae was investigated using the chromogenic substrate Phe-Pro-Ala-pNA. A 50 µl solution of enzyme was diluted in 50 µl of Britton-Robinson buffer at the indicated pH before incubation with 50 µl of Phe-Pro-Ala-pNA, adjusted to a final substrate concentration of 0.2 mM. The assays were performed in an UV-max kinetic microtiter plate reader (Molecular Devices) and the reaction followed for 3.5 min at 405 nm. The relative activity (RA) is given in Table 7 below.

TABLE 7

Effect of pH on TPAP activity

| pH | 4.0 | 4.5 | 5.0 | 5.5 | 6.0 | 6.5 | 7.0 | 7.5 | 8.0 | 8.5 | 9.0 |
|---|---|---|---|---|---|---|---|---|---|---|---|
| RA | 13 | 11 | 14 | 26 | 61 | 100 | 74 | 29 | 1 | 0 | 0 |

EXAMPLE 12
RNA isolation

Aspergillus oryzae strain 1568 (ATCC 20386) was cultivated in a fermentation tank in a medium comprised of 7.5 g of potato starch, 10 g of soy bean meal, 2 g of $KH_2PO_4$, 5 g of $Na_2HPO_4$-$2H_2O$, and 0.1 g of $ZnSO_4$-$7H_2O$ per liter. A two liter sample five days of growth at 30° C., and the mycelia were collected, frozen in liquid $N_2$, and stored at −80° C. Total RNA was prepared from the frozen, powdered mycelia of Aspergillus oryzae 1568 by extraction with guanidinium thiocyanate followed by ultracentrifugation through a 5.7M cesium chloride cushion (Chirgwin et al., 1979, Biochemistry 18:5294–5299). Poly(A)+ RNA was isolated by oligo(dT)-cellulose affinity chromatography according to Aviv and Leder (1972, Proceedings of the National Academy of Sciences USA 69:1408–1412).

EXAMPLE 13
Construction of a cDNA library

Double-stranded cDNA was synthesized from 5 µg of Aspergillus oryzae 1568 poly(A)+ RNA of Example 11 using the procedure described by Gubler and Hoffman (1983, Gene 25:263–269) and Sambrook et al. (1989, Molecular Cloning: A Laboratory Manual, Cold Spring Harbor Press, Cold Spring Harbor, N.Y.), except that an oligo(dT)-NotI anchor primer, instead of an oligo(dT)12–18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA was digested with NotI, size-fractionated for 1.2–3.0 kb cDNAs by agarose gel electrophoresis, and ligated into BstXI/NotI cleaved pYES2.0 vector (Invitrogen, San Diego, Calif.). The ligation mixture was transformed into electrocompetent E. coli DH10B cells (Life Technologies, Gaithersburg, Md.) according to the manufacturer's instructions. The library consisting of 1×10⁶ independent clones was stored as individual pools (25,000–30,000 colony forming units/pool) in 20% glycerol at −80° C., and as double stranded cDNA and ligation mixture at −20° C.

EXAMPLE 14
Genomic DNA Extraction

Aspergillus oryzae 1568 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia preparation which was subsequently frozen in liquid nitrogen. The frozen mycelia preparation was ground to a fine powder in an electric coffee grinder, and the powder was added to a disposable plastic centrifuge tube containing 20 ml of TE buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3M solution) was added to the extracted sample to a final concentration of 0.3M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 µg/ml and the mixture was then incubated at 37° C. for 30 minutes Proteinase K (200 µg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

EXAMPLE 15
PCR Amplification of Aspergillus oryzae 1568 tripeptide aminopeptidase Based on the amino acid sequences of the Aspergillus oryzae 1568 tripeptide aminopeptidase partial peptides described in WO 96/14404, the degenerate oligonucleotide primers shown below were synthesized with an Applied Biosystems Model 394 DNA/RNA Synthesizer, according to the manufacturer's instructions, for use to PCR amplify tripeptide aminopeptidase gene fragments from Aspergillus oryzae 1568:

Forward primer:
5'-TAYAAYATHGGIGAYTAYCARGCYGAYGC-3' (SEQ ID No. 20)

Reverse primer:
5'-GCIACIGCYTGRTTYTGCCAYTCIGG-3' (SEQ ID No. 21)

(R=A or G, Y=C or T, N=G or A or C or T, H=A or C or T, I=Inosine)

Amplification reactions (100 µl) were prepared using approximately 1 µg of genomic DNA isolated from an Aspergillus oryzae 1568 as described in Example 13 as the template. Each reaction contains the following components: 1 µg genomic DNA, 40 pmol forward primer, 40 pmol reverse primer, 200 µM each of dATP, dCTP, dGTP, and dTTP, 1×Taq polymerase buffer (Perkin-Elmer Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows: Cycle 1—95° C. for 5 minutes, 45° C. for 2 minutes, and 67° C. for 2 minutes; and Cycles 2-30—95° C. for 2 minutes; 45° C. for one minute, and 67° C. for 2 minutes. The reaction products were isolated on a 1% agarose gel (Eastman Kodak, Rochester, N.Y.). The 760 bp product band was excised from the gel and purified using GenElute spin columns (Supelco, Bellefonte, Pa.) according to the manufacturer's instructions. The purified PCR products were subsequently cloned into a pCRII vector (Invitrogen, San Diego, Calif.) and the DNA sequences were determined using lac forward and reverse primers (New England BioLabs, Beverly, Mass.).

A tripeptide aminopeptidase I gene segment (760 bp) consisting of 145 codons and interrupted by a 53 bp intron was amplified from *Aspergillus oryzae* 1568 with the tripeptide aminopeptidase-specific PCR primers described above. DNA sequence analysis shows that the amplified gene segment encodes a portion of the corresponding *Aspergillus oryzae* 1568 tripeptide aminopeptidase I gene. The tripeptide aminopeptidase I gene segment was used to probe an *Aspergillus oryzae* 1568 cDNA library.

EXAMPLE 16

Identification of tripeptide aminopeptidase I clones

The *Aspergillus oryzae* 1568 cDNA library was plated on Luria plus 50 μg/ml carbenicillin agar plates. Colony lifts (Maniatis et al., 1982, *Molecular Cloning, A Laboratory Manual*, Cold Spring Harbor Press, Cold Spring Harbor, N.Y.) were performed on approximately 5,000 colonies and the DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 mg/ml of denatured and sheared herring sperm DNA. The tripeptide aminopeptidase I gene fragment isolated from the *Aspergillus oryzae* 1568 as described in Example 13 was radiolabeled using the Random Primed DNA Labeling Kit (Boehringer Mannheim, Mannheim, Germany), denatured by adding NaOH to a final concentration of 0.1M, and added to the hybridization solution at an activity of approximately 1×10⁶ cpm per ml of hybridization solution. The mixture was incubated overnight at 45° C. in a shaking water bath. Following incubation, the membranes were washed once in 2×SSC with 0.2% SDS at 55° C. followed by two washes in 2×SSC at the same temperature. The membranes were dried on blotting paper for 15 minutes, wrapped in SaranWrap™, and exposed to X-ray film overnight at −70° C. with intensifying screens (Kodak, Rochester, N.Y.).

Two colonies, designated *E. coli* DH5α clones EJG13A and EJG13B, produced strong hybridization signals with the probe. The two colonies were inoculated into three ml of LB plus 50 μg/ml carbenicillin medium and grown overnight at 37° C. Miniprep DNA was prepared from each of these clones using the Wizard 373 DNA Purification Kit (Promega, Madison, Wis.). The tripeptide aminopeptidase encoding plasmids (pEJG13) were confirmed by DNA sequencing.

EXAMPLE 17

DNA sequence analysis of *Aspergillus oryzae* 1568 tripeptide aminopeptidase I gene DNA sequencing of the tripeptide aminopeptidase I gene contained on pEJG13 in *E. coli* DH5α EJG13A described in Example 15 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virology Methods* 38:47–60). Oligonucleotide sequencing primers were designed to complementary sequences in the tripeptide aminopeptidase I gene and were synthesized on an Applied Biosystems Model 394 DNA/RNA Synthesizer according to the manufacturer's instructions.

The nucleotide sequence of the gene encoding the *Aspergillus oryzae* 1568 tripeptide aminopeptidase I is shown in FIG. 2 (SEQ ID No. 18). Sequence analysis of the cloned insert revealed a large open reading frame of 1800 nucleotides (excluding the stop codon) encoding a protein of 600 amino acids sequence (SEQ ID No. 19). The G+C content of this open reading frame is 59.4%. Based on the rules of van Heijne (van Heijne, 1984, *Journal of Molecular Biology* 173:243–251), the first 21 amino acids likely comprise a secretory signal peptide which directs the nascent polypeptide into the endoplasmic reticulum. The next 179 amino acids likely comprise a propeptide.

The amino acid sequences of the partial peptides derived from the purified tripeptide aminopeptidase I as described in WO 96/14404 are boxed in FIG. 2 and are consistent with those found in the deduced amino acid sequence (SEQ ID No. 19) of the *Aspergillus oryzae* 1568 tripeptide aminopeptidase cDNA.

Using the Clustal alignment program (Higgins, 1989, supra) to compare the deduced amino acid sequence of the *Aspergillus oryzae* 1568 tripeptide aminopeptidase to that of the *Aspergillus niger* tripeptide aminopeptidase (SEQ ID No. 17), a 69.7% identity is observed (FIG. 3).

EXAMPLE 18

Construction of pEJG17 for expression of the *Aspergillus oryzae* 1568 tripeptide aminopeptidase I gene in Fusarium Two synthetic oligonucleotide primers shown below were designed to PCR amplify the *Aspergillus oryzae* 1568 tripeptideaminopeptidase I gene coding sequence from plasmid pEJG13 (*E. coli* DH5α EJG13A clone) for subcloning and expression in a Fusarium host.

SwaI
Forward Primer: 5'-GGG ATTTAAATATGTTCTTCAGTCGT-3' (SEQ ID No. 22)

PacI
Reverse primer: 5'-GGG TTAATTAATTAGTTGCCAAGGGC-3' (SEQ ID No. 23)

In order to facilitate the subcloning of the gene fragment into an expression vector designated pDM181 (FIG. 4), SwaI and PacI restriction enzyme sites were introduced at the 5' and 3' end of the gene, respectively. The vector pDM181 contained the *Fusarium oxysporum* (SP 387) trypsin-like protease promoter and terminator (WO 96/00787) as regulatory sequences. The plasmid also contained the bar gene as a selectable marker for fungal transformations.

Figure 5:
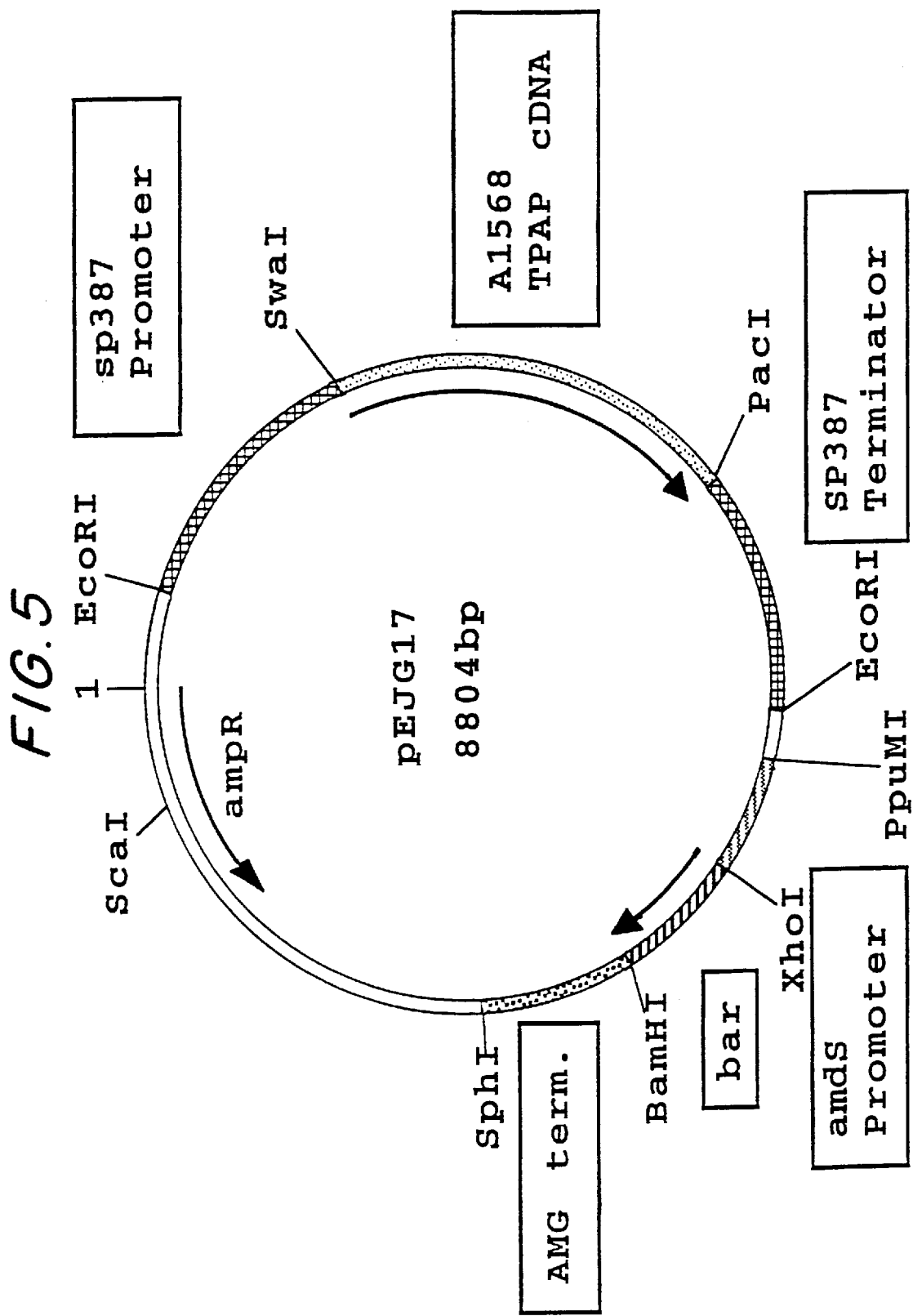
FIG. 5 shows a restriction map of pEJG17.

One hundred picomoles of each of the primers above were used in a PCR reaction containing 52 ng of pEJG13, 1×Pwo Buffer (Boehringer Mannheim, Indianapolis, Ind.), 1 mM each dATP, dTTP, dGTP, and dCTP, and 2.5 units of PwoI (Boehringer Mannheim, Indianapolis, Ind.). The amplification conditions were one cycle at 94° C. for 2 minutes, 50° C. for 30 seconds, and 72° C. for 1 minute; 9 cycles each at 94° C. for 15 seconds, 50° C. for 30 seconds, and 72° C. for 1 minute; 15 cycles each at 94° C. for 15 seconds, 55° C. for 30 seconds, and 72° C. for 1 minute plus 20 seconds for each additional cycle; one cycle at 94° C. for 15 seconds, 55° C. for 30 seconds, and 72° C. for 7 minutes; and a soak cycle at 4° C. The amplified 2866 bp DNA fragment was purified by gel electrophoresis and cut with restriction endonucleases SwaI and PacI (using conditions specified by the manufacturer). The cut fragment was cloned into pDM181 (FIG. 4) that had been previously cut with SwaI and PacI resulting in the expression plasmid pEJG17 (FIG. 5) in which transcription of the tripeptide aminopeptidase I gene was under the control of the the *Fusarium oxysporum* trypsin-like protease promoter. The plasmid pEJG17 was transformed into *E. coli* DH5α cells. The *E. coli* transformant containing the pEJG17 plasmid was isolated and plasmid DNA was prepared according to procedures described by Sambrook et al., 1989, supra.

EXAMPLE 19
Transformation of Fusarium

Fusarium strain CC1-3, a highly branched morphological mutant of Fusarium strain A3/5 (ATCC 20334) was grown in a liquid medium containing Vogel's salts, (Vogel, 1964, *Am. Nature* 98:435–446), 25 mM NaNO$_3$, and 1.5% glucose for 4 days at 28° C. and 150 rpm. Conidia were purified by filtration through 4 layers of cheesecloth and finally through one layer of Miracloth. Conidial suspensions were concentrated by centrifugation. Fifty ml of YPG medium comprised of 1% yeast extract, 2% bactopeptone, and 2% glucose were inoculated with approximately $10^8$ conidia, and incubated for 14 hours at 24° C. and 150 rpm. Resulting hyphae were trapped on a sterile 0.4 μm filter and washed successively with sterile distilled water and 1.0M MgSO$_4$. The hyphae were resuspended in 10 ml of NOVOZYM 234™ solution (2–10 mg/ml in 1.0M MgSO$_4$) and digested for 15–30 minutes at 34° with agitation at 80 rpm. Undigested hyphal material was removed from the resulting protoplast suspension by successive filtration through 4 layers of cheesecloth and through Miracloth. Twenty ml of 1M sorbitol were combined with the protoplast solution. After mixing, the protoplasts were pelleted by centrifugation and washed successively by resuspension and centrifugation in 20 ml of 1M sorbitol and in 20 ml of STC (0.8M sorbitol, 0.05M Tris pH 8.0, 0.05M CaCl$_2$). The washed protoplasts were resuspended in 4 parts STC and 1 part SPTC (0.8M sorbitol, 40% PEG 4000, 0.05M Tris pH 8.0, 0.05M CaCl$_2$) at a concentration of $5 \times 10^7$/ml. One hundred μl of protoplast suspension were added to 5 μg of pEJG17 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1×Vogel's salts (Vogel, 1964, *Am. Nature* 98:435–446), 25 mM NaNO$_3$, 0.8M sucrose and 1% low melting agarose (Sigma Chemical Company, St. Louis, Mo.) were mixed with the protoplasts and then plated onto an empty 100 mm petri plate. Incubation was continued at room temperature for 10 to 14 days. After incubation at room temperature for 24 hours, 12.5 ml of the identical medium plus 10 mg of basta (Hoechst Schering, Rodovre, Denmark) per ml were overlayed onto the Petri plate. Basta was extracted twice with phenol:chloroform:isoamyl alcohol (25:24:1), and once with chloroform:isoamyl alcohol (24:1) before use. After two weeks, ten transformants were apparent. A mycelial fragment from the edge of each transformant was transferred to individual wells of a 24 well plate containing Vogel's/BASTA medium. The medium contained 25 g of sucrose, 25 g of Noble agar, 20 mls of 50×Vogel's salts (Vogel, 1964, supra), 25 mM NaNO$_3$, and 10 g of basta per liter. The plate was sealed in a plastic bag to maintain moisture and incubated approximately one week at room temperature.

EXAMPLE 20
Expression of tripeptide aminopeptidase I gene

A mycelial fragment from each of the ten Fusarium CC1-3 transformants described in Example 18 was inoculated into 20 ml of M400 Da medium containing 50 g of maltodextrin, 2.0 g of MgSO$_4$-7H$_2$O, 2.0 g of KH$_2$PO$_4$, 4.0 g of citric acid, 8.0 g of yeast extract, 2.0 g of urea, and 0.5 ml of trace metals solution per liter and incubated for 7 days at 30° C. and 150 rpm. The medium was adjusted to pH 6.0 with 5N NaOH. The trace metals solution contained 14.3 g of ZnSO$_4$-7H$_2$O, 2.5 g of CuSO$_4$-5H$_2$O, 0.5 g of NiCl$_2$-6H$_2$O, 13.8 g of FeSO$_4$-7H$_2$O, 8.5 g of MnSO$_4$-H$_2$O, and 3.0 g of citric acid per liter. Aliquots were taken at days 5, 6, and 7 and assayed for tripeptide aminopeptidase activity according to the following assay. The untransformed host was also run as a control.

The stock substrate solution was prepared by dissolving 10 mg of Phe-Pro-Ala-p-nitrophenylacetate (Bachem, Inc., Torrance, Calif.) in 100 μl of DMSO and diluting the solution 50-fold in 50 mM sodium phosphate pH 7.5 buffer. The tripeptide aminopeptidase aliquots were diluted in 50 mM sodium phosphate pH 7.5 buffer. Then in a 96 well plate, 100 μl of each enzyme solution is mixed with 100 μl of the Phe-Pro-Ala-p-nitrophenylacetate solution and the absorbance at 405 nm is measured over a 3 minute period with a Molecular Devices ThermoMax microplate reader (Molecular Devices, Sunnyvale, Calif.).

The results of the tripeptide aminopeptidase assays demonstrated that 8 of the 10 transformants produced activity.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* DH5α pEJG13 | NRRL B-21617 | August 28, 1996 |

---

We claim:

1. An isolated tripeptidyl aminopeptidase which is encoded by a nucleic acid sequence selected from the group consisting of:
   (a) the nucleic acid sequence of SEQ ID No. 16, or its complementary strand;
   (b) a nucleic acid sequence, endogenous to an Aspergillus strain, comprising the amino-terminal tripeptidyl aminopeptidase encoding sequence comprised by plasmid pJaL406 and the carboxyl-terminal tripeptidyl aminopeptidase encoding sequence comprised by plasmid pJaL435;
   (c) a nucleic acid sequence, endogenous to an Aspergillus strain, which hybridizes with one or both of (i) SEQ ID NO: 16 and (ii) a nucleic acid sequence encoding the tripeptidyl aminopeptidase encoded by the amino-terminal tripeptidyl aminopeptidase encoding sequence comprised by plasmid pJaL406 and the carboxyl-terminal tripeptidyl aminopeptidase encoding sequence comprised by plasmid pJaL435, wherein the hybridization conditions have a stringency defined by overnight incubation at 45° C. in a solution of fivefold concentrated SSPE, 50% formamide and 0.3% SDS;
   (d) an allelic form of (a), (b) or (c); and
   (e) a fragment of (a), (b), (c) or (d) specifying an active tripeptidyl aminopeptidase.

2. The tripeptidyl aminopeptidase of claim 1 which is encoded by a nucleic acid sequence selected from the group consisting of:
   (a) a nucleic acid sequence comprising one or more of the nucleic acid sequences of SEQ ID No. 1, 2 and 3, or comprising the respective complementary strand;
   (b) a nucleic acid sequence which hybridizes with one or more of the sequences of SEQ ID No. 1, 2 and 3;
   (c) an allelic form of (a) or (b); and
   (d) a fragment of (a), (b) or (c) specifying an active tripeptidyl aminopeptidase.

3. An isolated tripeptidyl aminopeptidase of claim 1 which comprises one or both of the following characteristics:
   (a) the capacity to cleave the substrate Phe-Pro-Ala-pNA; and
   (b) an N-terminal sequence comprising the amino acid sequence set forth in SEQ ID NO: 15:
Ala-Xaa(1)-Asn-Xaa(2)-Ser-His-Cys-Asp-Ser-Ile-Ile-Thr-Pro-Xaa(3)-Cys-Leu-Lys-Xaa(4)-Leu-Tyr-Asn-Ile-Gly-Asp-Tyr-Gln-Ala-Asp-Xaa(5)-Xaa(6), in which any one of Xaa(1), Xaa(2), Xaa(3), Xaa(4), Xaa(5) and Xaa(6) may be different or identical and selected from any of the naturally occurring amino acid residues.

4. The tripeptidyl aminopeptidase of claim 3, in which Xaa(1) is Lys or Gln, Xaa(2) is Ile or Thr, Xaa(3) is Pro or His, Xaa(4) is Glu or Gln, Xaa(5) is Pro or Ala and Xaa(6) is Lys or Asn.

5. The tripeptidyl aminopeptidase of claim 1, which has a pH optimum in the range of 5.0–7.5.

6. The tripeptidyl aminopeptidase of claim 1 which is endogenous to a strain of A. oryzae.

7. The tripeptidyl aminopeptidase of claim 1 which is endogenous to a strain of A. niger.

8. The tripeptidyl aminopeptidase of claim 1 which is endogenous to a strain of A. japonicus.

9. The tripeptidyl aminopeptidase of claim 1 which is endogenous to a strain of A. foetidus.

10. An isolated DNA sequence encoding a tripeptidyl aminopeptidase of claim 1.

11. An isolated DNA sequence encoding a tripeptidyl aminopeptidase of claim 2.

12. A DNA construct comprising the DNA sequence of claim 10.

13. An expression vector comprising the DNA sequence of claim 10.

14. A host cell comprising a DNA sequence of claim 10.

15. A method of producing tripeptidyl aminopeptidase comprising culturing a host cell of claim 14 under conditions for the expression of the tripeptidyl aminopeptidase, and recovering tripeptidyl aminopeptidase from the culture.

16. A method of producing a desired protein or peptide product comprising
   (a) modifying a DNA sequence capable of expressing a tripeptidyl aminopeptidase of claim 1 to inactivate the expression of the encoded tripeptidyl aminopeptidase,
   (b) transforming a cell capable of producing a desired protein or peptide product with the modified DNA sequence of clause (a) under conditions permitting homologous recombination between said modified DNA sequence and a cellular DNA sequence encoding an endogenous tripeptidyl aminopeptidase,
   (c) culturing said transformed cell capable of producing the desired protein or peptide product under conditions suitable for the production of the product, and,
   (d) recovering the desired product from the cell culture or from the cells.

17. A method of producing a desired protein or peptide product comprising
   (a) preparing a DNA construct capable of expressing a polynucleotide complementary to a DNA sequence encoding a tripeptidyl aminopeptidase of claim 1 said polynucleotide capable of hybridizing with a cellular mRNA specifying a tripeptidyl aminopeptidase,
   (b) transforming a cell capable of producing a desired protein or peptide product with the DNA construct of clause (a) under conditions permitting expression of said complementary polynucleotide and the intracellular hybridization of said complementary polynucleotide with a cellular mRNA specifying a tripeptidyl aminopeptidase,
   (c) culturing said transformed cell capable of producing the desired protein or peptide product under conditions suitable for the production of the product, and,
   (d) recovering the desired product from the cell culture or from the cells.

18. A method of reducing or eliminating the production of the tripeptidyl aminopeptidase of claim 1 in a cell, comprising introducing into the cell a nucleotide sequence which hybridizes with the mRNA produced during transcription of the DNA sequence encoding the tripeptidyl aminopeptidase.

19. A cell produced by the method of claim 18.

20. A method of producing a desired protein or peptide product comprising (a) culturing a cell capable of producing both the desired protein or peptide product and a tripeptidyl aminopeptidase of claim 1 in the presence of an effective amount of an inhibitor capable of inhibiting the activity of said tripeptidyl aminopeptidase, and, (b) recovering the desired protein or peptide product from the cell culture or from the cells.

\* \* \* \* \*

UNITED STATES PATENT AND TRADEMARK OFFICE
CERTIFICATE OF CORRECTION

PATENT NO. : 5,821,104

DATED : October 13, 1998

INVENTOR(S) : Holm et al.

It is certified that error appears in the above-identified patent and that said Letters Patent is hereby corrected as shown below:

Col. 15, line 32: delete "1250" and insert --250--
Col. 16, line 32: delete "1170" and insert --170--
Col. 16, line 55: delete "Gin" and insert --Gln--
Col. 20, lines 25-29, last column of Table 5, under 42, insert --<1--
                                                                                 insert -- - --
                                                                                 insert --<1--
                                                                                 insert --<1--
                                                                                 insert -- - --

Signed and Sealed this

Fourteenth Day of September, 1999

Attest:

Q. TODD DICKINSON

*Attesting Officer*      *Acting Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
  ( A ) LENGTH: 907 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1:

| | | | | | | |
|---|---|---|---|---|---|---|
| CACTGTCTGA | AGCAGCTGTA | CAACATCGGT | GACTACCAGG | CCGATCCCAA | GTCCGGCAGC | 60 |
| AAGATCGGCT | TTGCCAGCTA | CCTTGAGGAA | TACGCCCGGT | ATGCCGATCT | CGAGAGGTTC | 120 |
| GAGCAGCACC | TGGCTCCCAA | TGCCATCGGC | CAGAACTTCA | GCGTCGTCCA | ATTCAACGGC | 180 |
| GGCCTCAACG | ATCAGCTTTC | ATCGAGTGAC | AGCGGCGAAG | CCAACCTCGA | CCTGCAGTAC | 240 |
| ATCCTGGGCG | TCAGCGCTCC | CGTCCCCATC | ACCGAGTACA | GCACCGGCGG | ACGCGGCGAA | 300 |
| CTAGTCCCCG | ACCTGAGCTC | CCCCGACCCC | AACGACAACA | GCAACGAGCC | CTACCTTGAC | 360 |
| TTCCTTCAGG | GAATCCTCAA | GCTTAACAAC | TCCGACCTCC | CACAAGTCAT | CTCTACCTCC | 420 |
| TACGGTGAAG | ACGAACAGGT | ATGCACCTCA | CCTGACCCAT | TCCATTTTAC | ATCCCTCACC | 480 |
| TCTCTCAACC | AAACTAACAA | CACCAACAGA | CTATCCCCGT | CCCCTACGCC | CGCACCGTCT | 540 |
| GCAACCTCTA | CGCCCAACTC | GGCAGCCGCG | GCGTCTCTGT | AATCTTCTCC | AGCGGCGACT | 600 |
| CCGGCGTCGG | CGCCGCCTGC | CTCACCAACG | ACGGCACCAA | CCGCACGCAC | TTCCCTCCTC | 660 |
| AATTCCCCGC | CTCCTGCCCC | TGGGTAACCT | CCGTCGGCGC | AACCTCCAAG | ACCTCCCCCG | 720 |
| AGCAAGCCGT | CTCCTTCTCC | TCCGGCGGCT | TCTCCGACCT | CTGGCCCCGC | CCCTCCTACC | 780 |
| AACACGCCGC | CGTGCAAACC | TACCTCACCA | AGCACCTGGG | CAACAAGTTC | TCGGGGCTTT | 840 |
| TCAACGCCTC | CGGCCGCGCC | TTCCCCGACG | CTCCGCGCAG | GGCGTCAACT | ACGCTGTTTA | 900 |
| CGACAAA | | | | | | 907 |

( 2 ) INFORMATION FOR SEQ ID NO:2:

( i ) SEQUENCE CHARACTERISTICS:
    ( A ) LENGTH: 228 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

| | | | | | | |
|---|---|---|---|---|---|---|
| CACTGTCTGA | AGCAGCTGTA | CAACATCGGT | GACTACCAGG | CCGATCCCAA | GTCCGGCAGC | 60 |
| AAGATCGGCT | TGGGCAGCTA | CCTTGAGGAA | TACGCCCGGT | ATGCCGATCT | CGAGAGGTTC | 120 |
| GAGCAGCACC | TGGCTCCAAT | GCATCGGCAG | AACTCAGCGT | CGTCCAATTC | ACGGCGGCTC | 180 |
| ACGATCAGCT | TCATCGAGTG | ACAGCGGCGA | GCAACTCGAC | TGCAGTAC | | 228 |

( 2 ) INFORMATION FOR SEQ ID NO:3:

( i ) SEQUENCE CHARACTERISTICS:
    ( A ) LENGTH: 134 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| CCTCCTACCA | ACACGCCGCC | GTGCAACCTA | CCTGACCAAG | CACCTGGCAA | CAAGTTCTCG | 60 |
| GGGCTTTTCA | ACGCCTCCGG | CCGCGCCTTC | CCCGACGTCT | CCGCGCAGGG | CGTCAACTAC | 120 |
| GCTGTTTACG | ACAA | | | | | 134 |

( 2 ) INFORMATION FOR SEQ ID NO:4:

( i ) SEQUENCE CHARACTERISTICS:
- ( A ) LENGTH: 30 amino acids
- ( B ) TYPE: amino acid
- ( C ) STRANDEDNESS: single
- ( D ) TOPOLOGY: linear ( i i ) MOLECULE TYPE: None ( x i ) SEQUENCE DESCRIPTION: SEQ ID NO:4:

Ala Gln Asn Thr Ser His Cys Asp Ser Ile Ile Thr Pro His Cys Leu
 1               5                   10                  15
Lys Gln Leu Tyr Asn Ile Gly Asp Tyr Gln Ala Asp Pro Lys
                20                  25                  30

( 2 ) INFORMATION FOR SEQ ID NO:5:

( i ) SEQUENCE CHARACTERISTICS:
- ( A ) LENGTH: 25 amino acids
- ( B ) TYPE: amino acid
- ( C ) STRANDEDNESS: single
- ( D ) TOPOLOGY: linear ( i i ) MOLECULE TYPE: None ( x i ) SEQUENCE DESCRIPTION: SEQ ID NO:5:

Thr Ser Pro Glu Gln Ala Val Ser Phe Ser Ser Gly Gly Phe Ser Asp
 1               5                   10                  15
Leu Trp Pro Arg Pro Ser Tyr Gln His
                20                  25

( 2 ) INFORMATION FOR SEQ ID NO:6:

( i ) SEQUENCE CHARACTERISTICS:
- ( A ) LENGTH: 27 amino acids
- ( B ) TYPE: amino acid
- ( C ) STRANDEDNESS: single
- ( D ) TOPOLOGY: linear ( i i ) MOLECULE TYPE: None ( x i ) SEQUENCE DESCRIPTION: SEQ ID NO:6:

Phe Ser Gly Leu Phe Asn Ala Ser Gly Arg Ala Phe Pro Asp Val Ser
 1               5                   10                  15
Ala Gln Gly Val Asn Tyr Ala Val Tyr Asp Lys
                20                  25

( 2 ) INFORMATION FOR SEQ ID NO:7:

( i ) SEQUENCE CHARACTERISTICS:
- ( A ) LENGTH: 23 amino acids
- ( B ) TYPE: amino acid
- ( C ) STRANDEDNESS: single
- ( D ) TOPOLOGY: linear ( i i ) MOLECULE TYPE: None ( x i ) SEQUENCE DESCRIPTION: SEQ ID NO:7:

Ile Gly Phe Ala Ser Tyr Leu Gln Glu Tyr Ala Arg Tyr Ala Asx Leu
 1               5                   10                  15
Glu Arg Phe Glu Gln His Leu
                20

( 2 ) INFORMATION FOR SEQ ID NO:8:

( i ) SEQUENCE CHARACTERISTICS:
- ( A ) LENGTH: 29 amino acids
- ( B ) TYPE: amino acid (C) STRANDEDNESS: single
(D) TOPOLOGY: linear (ii) MOLECULE TYPE: None (xi) SEQUENCE DESCRIPTION: SEQ ID NO:8:

```
Xaa Leu Asx Leu Gln Tyr Ile Leu Gly Val Ser Ala Pro Val Pro Ile
 1               5                  10                  15
Thr Glu Tyr Ser Thr Gly Gly Arg Gly Glu Leu Val Pro
             20                  25
```

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Gly Ala Leu Asx Asp Ile Val Asn Gly Thr Ser Val Gly Gln Asp Gly
 1               5                  10                  15
Arg Asn Arg Phe Gly Gly Thr Pro Asn Gly Ser
             20                  25
```

(2) INFORMATION FOR SEQ ID NO:10:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

```
Glu Leu Tyr Asn Ile Gly Asp Tyr Gln Ala Asp Ala Asn Ser Gly Ser
 1               5                  10                  15
Lys
```

(2) INFORMATION FOR SEQ ID NO:11:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Thr Thr Pro Glu Arg Gly Thr Tyr Phe Ser Ser Gly Gly Phe Ser Asn
 1               5                  10                  15
Tyr Trp Pro Arg Pro Glu Trp Gln Asn Gln Ala Val Ala Ser Tyr Leu
             20                  25                  30
```

(2) INFORMATION FOR SEQ ID NO:12:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: None ( x i ) SEQUENCE DESCRIPTION: SEQ ID NO:12:

| Gly | Thr | Leu | Gly | Glu | Phe | Asp | Gly | Thr | Ser | Ala | Ser | Ala | Pro | Ala | Phe |
| 1 | | | | 5 | | | | | 10 | | | | | 15 | |

| Ser | Ala | Val | Ile | Ala | Leu | Leu | Asn | Asp | Ala | Arg | Leu | Arg | Ala | Gly | Lys |
| | | | 20 | | | | | 25 | | | | | 30 | | |

| Pro | Thr | Leu | Gly | Phe | Leu | Asn | Pro | Trp | Leu | Tyr | Lys |
| | | 35 | | | | | 40 | | | | |

( 2 ) INFORMATION FOR SEQ ID NO:13:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:13:

| Thr | Gly | Arg | Gln | Gly | Leu | Gln | Asn | Ile | Thr | Leu | Gly | Ala | Ser | Ile | Gly |
| 1 | | | | 5 | | | | | 10 | | | | | 15 | |

| Xaa | Thr | Gly | Arg | Ala | Arg | Phe | Gly | Gly | Ala | Pro | Asn | Gly | Gly | Pro | Val |
| | | | 20 | | | | | 25 | | | | | 30 | | |

| Val | Pro | Tyr | Ala | Ser |
| | | | 35 | |

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:14:

| Ala | Lys | Xaa | Ile | Ser | His | Tyr | Asp | Ser | Ile | Ile | Thr | Pro | Pro | Tyr | Leu |
| 1 | | | | 5 | | | | | 10 | | | | | 15 | |

| Lys | Glu | Leu | Tyr | Asn | Ile | Gly |
| | | | 20 | | | |

( 2 ) INFORMATION FOR SEQ ID NO:15:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:15:

| Ala | Xaa | Asn | Xaa | Ser | His | Cys | Asp | Ser | Ile | Ile | Thr | Pro | Xaa | Cys | Leu |
| 1 | | | | 5 | | | | | 10 | | | | | 15 | |

| Lys | Xaa | Leu | Tyr | Asn | Ile | Gly | Asp | Tyr | Gln | Ala | Asp | Xaa | Xaa |
| | | | 20 | | | | | 25 | | | | | 30 |

( 2 ) INFORMATION FOR SEQ ID NO:16:

( i ) SEQUENCE CHARACTERISTICS:
        ( A ) LENGTH: 2424 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ACATGGCAGT CTTAATCGCC TGCAGCGGCA GTAATGATAG TCCTGCCGGC GAATAATAAC      60
CCCATAACAA ACAAATAAAT AATACTACTT ATCTCTCCTC GTCCCTTTAA CTTTCCCTTT     120
GCCGTCTTCA ATCCCTCAT  CTTGGTCTCT TCGGCAGCCT TTCACCATGC TGTCGTCTCT     180
CCTTAGCCAG GGAGCAGCCG TATCCCTCGC GGTGTTGTCG CTGCTCCCTT CGCCTGTAGC     240
CGCGGAGATC TTCGAAAAGC TATCCGGCGT CCCCAATGGT GAGTTATAGA CCCCAATTCT     300
TCATTTTGAG CCACATACTG ACGTGATTCC TTCGAATACT ACCAGGCTGG AGATACGCCA     360
ACAATCCTCA AGGCAACGAG GTCATTCGCT TGCAAATCGC CCTTCAGCAG CATGATGTCG     420
CTGGTTTCGA ACAAGCCGTG ATGGATATGT CCACCCCCGG ACACGCCGAC TATGGAAAGC     480
ATTTCCGCAC CCACGATGAG ATGAAGCGCA TGTTGCTCCC CAGCGAGACT GCCGTCGACT     540
CAGTCCGCGA CTGGCTGGAA TCCGCCGGTG TCCACAATAT CCAGGTCGAC GCCGACTGGG     600
TCAAGTTCCA TACCACCGTA AACAAGGCCA ATGCCCTGCT GGATGCCGAC TTCAAGTGGT     660
ATGTCAGCGA CGCCAAGCAT ATTCGTCGTC TGCGCACCCT GCAATACTCC ATCCCCGACG     720
CCCTGGTCTC GCACATCAAC ATGATCCAGC CCACCACCCG CTTTGGCCAG ATCCAGCCCA     780
ACCGTGCCAC CATGCGCAGC AAGCCCAAGC ACGCCGATGA GACATTCCTC ACCGCAGCCA     840
CCCTGGCCCA GAACACCTCC CACTGCGACT CCATCATCAC ACCGCACTGT CTGAAGCAGC     900
TGTACAACAT CGGTGACTAC CAGGCCGATC CCAAGTCCGG CAGCAAGATC GGCTTTGCCA     960
GCTACCTTGA GGAATACGCC CGGTATGCCG ATCTCGAGAG GTTCGAGCAG CACCTGGCTC    1020
CCAATGCCAT CGGCCAGAAC TTCAGCGTCG TCCAATTCAA CGGCGGCCTC AACGATCAGC    1080
TTTCATCGAG TGACAGCGGC GAAGCCAACC TCGACCTGCA GTACATCCTG GGCGTCAGCG    1140
CTCCCGTCCC CATCACCGAG TACAGCACCG GCGGACGCGG CGAACTAGTC CCCGACCTGA    1200
GCTCCCCCGA CCCCAACGAC AACAGCAACG AGCCCTACCT TGACTTCCTT CAGGGAATCC    1260
TCAAGCTTAA CAACTCCGAC CTCCCACAAG TCATCTCTAC CTCCTACGGT GAAGACGAAC    1320
AGGTATGCAC CTCACCTGAC CCATTCCATT TTACATCCCT CACCTCTCTC AACCAAACTA    1380
ACAACACCAA CAGACTATCC CCGTCCCCTA CGCCCGCACC GTCTGCAACC TCTACGCCCA    1440
ACTCGGCAGC CGCGGCGTCT CTGTAATCTT CTCCAGCGGC GACTCCGGCG TCGGCGCCGC    1500
CTGCCTCACC AACGACGGCA CCAACCGCAC GCACTTCCCT CCTCAATTCC CCGCCTCCTG    1560
CCCCTGGGTA ACCTCCGTCG GCGCAACCTC CAAGACTTCC CCCGAGCAAG CCGTCTCCTT    1620
CTCCTCCGGC GGCTTCTCCG ACCTCTGGCC CCGCCCCTCC TACCAACACG CCGCCGTGCA    1680
AACCTACCTC ACCAAGCACC TGGGCAACAA GTTCTCGGGG CTTTTCAACG CCTCCGGCCG    1740
CGCCTTCCCC GACGTCTCCG CGCAGGGCGT CAACTACGCT GTTTACGACA AGGGCATGCT    1800
TGGCCAGTTC GACGGGACGA GTTGCTCCGC GCCGACGTTC AGTGGCGTCA TCGCGTTGTT    1860
GAACGATGCG AGACTGAGGG CCGGGTTGCC TGTGATGGGG TTCTTGAATC CGTTCCTGTA    1920
TGGTGTCGGA AGTGAGAAGG GTGCGTTGAA TGATATTGTG AACGGCGGGA GTGTGGGTTG    1980
TGATGGGAGG AATCGGTTCG GGGGCACGCC TAATGGTAGT CCTGTTGTGC CGTTTGCTAG    2040
TTGGAATGCC ACGACCGGGT GGGATCCTGT GTCGGGGTTG GGAACGCCGG ATTTTGCGAA    2100
GTTGAAAGGG GTGGCGTTGG GTGAGGAGGG TGGTAATTAA GTGTGAGATG GGGGAAAGG     2160
GATTTCTTT  TCGATGTGAA TATTAGGTGA ATTGTGTGGA TAATTTTCAT ACATAATTAA    2220
GTCTGCATTG GCAGTGATAA CCTGGAAGAA ATGTCTAATG AGTGTGATTT GTTACTTAT     2280
GTATATTGAG TAATGGAATG TAGATGACTT GTCTTTGTAC TGTATAACGA AATGATTATT    2340
```

```
TGAGTGGAGG GTATTAAAGA ACTATAAAAT ATATACAAAG GTTAACCCAT GCAGTCGTAA      2400

CCCATAATGC AAAGCTCTAC TCTA                                            2424
```

( 2 ) INFORMATION FOR SEQ ID NO:17:

( i ) SEQUENCE CHARACTERISTICS:
        ( A ) LENGTH: 611 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
Met Leu Ser Ser Leu Leu Ser Gln Gly Ala Ala Val Ser Leu Ala Val
 1               5                  10                  15

Leu Ser Leu Leu Pro Ser Pro Val Ala Ala Glu Ile Phe Glu Lys Leu
                20                  25                  30

Ser Gly Val Pro Asn Gly Trp Arg Tyr Ala Asn Asn Pro Gln Gly Asn
            35                  40                  45

Glu Val Ile Arg Leu Gln Ile Ala Leu Gln Gln His Asp Val Ala Gly
        50                  55                  60

Phe Glu Gln Ala Val Met Asp Met Ser Thr Pro Gly His Ala Asp Tyr
 65                  70                  75                  80

Gly Lys His Phe Arg Thr His Asp Glu Met Lys Arg Met Leu Leu Pro
                85                  90                  95

Ser Glu Thr Ala Val Asp Ser Val Arg Asp Trp Leu Glu Ser Ala Gly
                100                 105                 110

Val His Asn Ile Gln Val Asp Ala Asp Trp Val Lys Phe His Thr Thr
            115                 120                 125

Val Asn Lys Ala Asn Ala Leu Leu Asp Ala Asp Phe Lys Trp Tyr Val
        130                 135                 140

Ser Asp Ala Lys His Ile Arg Arg Leu Arg Thr Leu Gln Tyr Ser Ile
145                 150                 155                 160

Pro Asp Ala Leu Val Ser His Ile Asn Met Ile Gln Pro Thr Thr Arg
                165                 170                 175

Phe Gly Gln Ile Gln Pro Asn Arg Ala Thr Met Arg Ser Lys Pro Lys
                180                 185                 190

His Ala Asp Glu Thr Phe Leu Thr Ala Ala Thr Leu Ala Gln Asn Thr
            195                 200                 205

Ser His Cys Asp Ser Ile Ile Thr Pro His Cys Leu Lys Gln Leu Tyr
        210                 215                 220

Asn Ile Gly Asp Tyr Gln Ala Asp Pro Lys Ser Gly Ser Lys Ile Gly
225                 230                 235                 240

Phe Ala Ser Tyr Leu Glu Glu Tyr Ala Arg Tyr Ala Asp Leu Glu Arg
                245                 250                 255

Phe Glu Gln His Leu Ala Pro Asn Ala Ile Gly Gln Asn Phe Ser Val
            260                 265                 270

Val Gln Phe Asn Gly Gly Leu Asn Asp Gln Leu Ser Ser Ser Asp Ser
        275                 280                 285

Gly Glu Ala Asn Leu Asp Leu Gln Tyr Ile Leu Gly Val Ser Ala Pro
        290                 295                 300

Val Pro Ile Thr Glu Tyr Ser Thr Gly Gly Arg Gly Glu Leu Val Pro
305                 310                 315                 320

Asp Leu Ser Ser Pro Asp Pro Asn Asp Asn Ser Asn Glu Pro Tyr Leu
                325                 330                 335

Asp Phe Leu Gln Gly Ile Leu Lys Leu Asn Asn Ser Asp Leu Pro Gln
                340                 345                 350
```

| | | | | | | | | | | | | | | |
|---|---|---|---|---|---|---|---|---|---|---|---|---|---|---|
|Val|Ile|Ser<br>355|Thr|Ser|Tyr|Gly|Glu<br>360|Asp|Glu|Gln|Thr|Ile<br>365|Pro|Val|Pro|
|Tyr|Ala<br>370|Arg|Thr|Val|Cys|Asn<br>375|Leu|Tyr|Ala|Gln|Leu<br>380|Gly|Ser|Arg|Gly|
|Val<br>385|Ser|Val|Ile|Phe|Ser<br>390|Ser|Gly|Asp|Ser|Gly<br>395|Val|Gly|Ala|Ala|Cys<br>400|
|Leu|Thr|Asn|Asp|Gly<br>405|Thr|Asn|Arg|Thr|His<br>410|Phe|Pro|Pro|Gln|Phe<br>415|Pro|
|Ala|Ser|Cys|Pro<br>420|Trp|Val|Thr|Ser|Val<br>425|Gly|Ala|Thr|Ser|Lys<br>430|Thr|Ser|
|Pro|Glu|Gln<br>435|Ala|Val|Ser|Phe|Ser<br>440|Ser|Gly|Gly|Phe|Ser<br>445|Asp|Leu|Trp|
|Pro|Arg<br>450|Pro|Ser|Tyr|Gln|His<br>455|Ala|Ala|Val|Gln|Thr<br>460|Tyr|Leu|Thr|Lys|
|His<br>465|Leu|Gly|Asn|Lys|Phe<br>470|Ser|Gly|Leu|Phe|Asn<br>475|Ala|Ser|Gly|Arg|Ala<br>480|
|Phe|Pro|Asp|Val|Ser<br>485|Ala|Gln|Gly|Val|Asn<br>490|Tyr|Ala|Val|Tyr|Asp<br>495|Lys|
|Gly|Met|Leu|Gly<br>500|Gln|Phe|Asp|Gly|Thr<br>505|Ser|Cys|Ser|Ala|Pro<br>510|Thr|Phe|
|Ser|Gly|Val<br>515|Ile|Ala|Leu|Leu|Asn<br>520|Asp|Ala|Arg|Leu|Arg<br>525|Ala|Gly|Leu|
|Pro|Val<br>530|Met|Gly|Phe|Leu|Asn<br>535|Pro|Phe|Leu|Tyr|Gly<br>540|Val|Gly|Ser|Glu|
|Lys<br>545|Gly|Ala|Leu|Asn|Asp<br>550|Ile|Val|Asn|Gly|Gly<br>555|Ser|Val|Gly|Cys|Asp<br>560|
|Gly|Arg|Asn|Arg|Phe<br>565|Gly|Gly|Thr|Pro|Asn<br>570|Gly|Ser|Pro|Val|Val<br>575|Pro|
|Phe|Ala|Ser|Trp<br>580|Asn|Ala|Thr|Thr|Gly<br>585|Trp|Asp|Pro|Val|Ser<br>590|Gly|Leu|
|Gly|Thr|Pro<br>595|Asp|Phe|Ala|Lys|Leu<br>600|Lys|Gly|Val|Ala|Leu<br>605|Gly|Glu|Glu|
|Gly|Gly|Asn<br>610| | | | | | | | | | | | | |

( 2 ) INFORMATION FOR SEQ ID NO:18:

( i ) SEQUENCE CHARACTERISTICS:
        ( A ) LENGTH: 1803 base pairs
        ( B ) TYPE: nucleic acid
        ( C ) STRANDEDNESS: single
        ( D ) TOPOLOGY: linear ( i i ) MOLECULE TYPE: Genomic DNA ( i x ) FEATURE:
        ( A ) NAME/KEY: Coding Sequence
        ( B ) LOCATION: 1...1800
        ( D ) OTHER INFORMATION:

( x i ) SEQUENCE DESCRIPTION: SEQ ID NO:18:

| | | | | | | | | | | | | | | | |
|---|---|---|---|---|---|---|---|---|---|---|---|---|---|---|---|
|ATG|TTC|TTC|AGT|CGT|GGA|GCG|CTT|TCG|CTC|GCA|GTG|CTT|TCA|CTG|CTC|48|
|Met|Phe|Phe|Ser|Arg|Gly|Ala|Leu|Ser|Leu|Ala|Val|Leu|Ser|Leu|Leu| |
|1| | | |5| | | | |10| | | | |15| | |
|AGC|TCC|TCC|GCC|GCA|GGG|GAG|GCT|TTT|GAG|AAG|CTG|TCT|GCC|GTT|CCA|96|
|Ser|Ser|Ser|Ala|Ala|Gly|Glu|Ala|Phe|Glu|Lys|Leu|Ser|Ala|Val|Pro| |
| | | |20| | | | |25| | | | |30| | | |
|AAG|GGA|TGG|CAC|TAT|TCT|AGT|ACC|CCT|AAA|GGC|AAC|ACT|GAG|GTT|TGT|144|
|Lys|Gly|Trp|His|Tyr|Ser|Ser|Thr|Pro|Lys|Gly|Asn|Thr|Glu|Val|Cys| |

|  |  |  |  |  |  |  |  |  |  |  |  |  |  |  |  |  |
|---|---|---|---|---|---|---|---|---|---|---|---|---|---|---|---|---|
|  | 35 |  |  |  |  | 40 |  |  |  |  |  | 45 |  |  |  |  |
| CTG | AAG | ATC | GCC | CTC | GCG | CAG | AAG | GAT | GCT | GCT | GGG | TTC | GAA | AAG | ACC | 192 |
| Leu | Lys | Ile | Ala | Leu | Ala | Gln | Lys | Asp | Ala | Ala | Gly | Phe | Glu | Lys | Thr |  |
|  | 50 |  |  |  | 55 |  |  |  |  | 60 |  |  |  |  |  |  |
| GTC | TTG | GAG | ATG | TCG | GAT | CCC | GAC | CAC | CCC | AGC | TAC | GGC | CAG | CAC | TTC | 240 |
| Val | Leu | Glu | Met | Ser | Asp | Pro | Asp | His | Pro | Ser | Tyr | Gly | Gln | His | Phe |  |
| 65 |  |  |  | 70 |  |  |  | 75 |  |  |  |  |  |  | 80 |  |
| ACC | ACC | CAC | GAC | GAG | ATG | AAG | CGC | ATG | CTT | CTT | CCC | AGA | GAT | GAC | ACC | 288 |
| Thr | Thr | His | Asp | Glu | Met | Lys | Arg | Met | Leu | Leu | Pro | Arg | Asp | Asp | Thr |  |
|  |  |  |  | 85 |  |  |  |  | 90 |  |  |  |  | 95 |  |  |
| GTT | GAT | GCC | GTT | CGA | CAA | TGG | CTC | GAA | AAC | GGC | GGC | GTG | ACC | GAC | TTT | 336 |
| Val | Asp | Ala | Val | Arg | Gln | Trp | Leu | Glu | Asn | Gly | Gly | Val | Thr | Asp | Phe |  |
|  |  |  | 100 |  |  |  |  | 105 |  |  |  |  | 110 |  |  |  |
| ACC | CAG | GAT | GCC | GAC | TGG | ATC | AAC | TTC | TGT | ACT | ACC | GTC | GAT | ACC | GCG | 384 |
| Thr | Gln | Asp | Ala | Asp | Trp | Ile | Asn | Phe | Cys | Thr | Thr | Val | Asp | Thr | Ala |  |
|  |  |  | 115 |  |  |  |  | 120 |  |  |  |  | 125 |  |  |  |
| AAC | AAA | CTC | TTG | AAT | GCC | CAG | TTC | AAA | TGG | TAC | GTC | AGC | GAT | GTG | AAG | 432 |
| Asn | Lys | Leu | Leu | Asn | Ala | Gln | Phe | Lys | Trp | Tyr | Val | Ser | Asp | Val | Lys |  |
|  | 130 |  |  |  |  | 135 |  |  |  |  | 140 |  |  |  |  |  |
| CAC | ATC | CGC | CGT | CTC | AGA | ACA | CTG | CAG | TAC | GAC | GTC | CCC | GAG | TCG | GTC | 480 |
| His | Ile | Arg | Arg | Leu | Arg | Thr | Leu | Gln | Tyr | Asp | Val | Pro | Glu | Ser | Val |  |
| 145 |  |  |  |  | 150 |  |  |  |  | 155 |  |  |  |  | 160 |  |
| ACC | CCT | CAC | ATC | AAC | ACC | ATC | CAA | CCG | ACC | ACC | CGT | TTT | GGC | AAG | ATT | 528 |
| Thr | Pro | His | Ile | Asn | Thr | Ile | Gln | Pro | Thr | Thr | Arg | Phe | Gly | Lys | Ile |  |
|  |  |  |  | 165 |  |  |  |  | 170 |  |  |  |  | 175 |  |  |
| AGC | CCC | AAG | AAG | GCC | GTT | ACC | CAC | AGC | AAG | CCC | TCC | CAG | TTG | GAC | GTG | 576 |
| Ser | Pro | Lys | Lys | Ala | Val | Thr | His | Ser | Lys | Pro | Ser | Gln | Leu | Asp | Val |  |
|  |  |  | 180 |  |  |  |  | 185 |  |  |  |  | 190 |  |  |  |
| ACC | GCC | CTT | GCT | GCC | GCT | GTC | GTT | GCA | AAG | AAC | ATC | TCG | CAC | TGT | GAT | 624 |
| Thr | Ala | Leu | Ala | Ala | Ala | Val | Val | Ala | Lys | Asn | Ile | Ser | His | Cys | Asp |  |
|  |  |  | 195 |  |  |  |  | 200 |  |  |  |  | 205 |  |  |  |
| TCT | ATC | ATT | ACC | CCC | ACC | TGT | CTG | AAG | GAG | CTT | TAC | AAC | ATT | GGT | GAT | 672 |
| Ser | Ile | Ile | Thr | Pro | Thr | Cys | Leu | Lys | Glu | Leu | Tyr | Asn | Ile | Gly | Asp |  |
|  | 210 |  |  |  |  | 215 |  |  |  |  | 220 |  |  |  |  |  |
| TAC | CAG | GCC | GAT | GCA | AAC | TCG | GGC | AGC | AAG | ATC | GCC | TTC | GCC | AGC | TAT | 720 |
| Tyr | Gln | Ala | Asp | Ala | Asn | Ser | Gly | Ser | Lys | Ile | Ala | Phe | Ala | Ser | Tyr |  |
| 225 |  |  |  |  | 230 |  |  |  |  | 235 |  |  |  |  | 240 |  |
| CTG | GAG | GAG | TAC | GCG | CGC | TAC | GCT | GAC | CTG | GAG | AAC | TTT | GAG | AAC | TAC | 768 |
| Leu | Glu | Glu | Tyr | Ala | Arg | Tyr | Ala | Asp | Leu | Glu | Asn | Phe | Glu | Asn | Tyr |  |
|  |  |  |  | 245 |  |  |  |  | 250 |  |  |  |  | 255 |  |  |
| CTT | GCT | CCC | TGG | GCT | AAG | GGC | CAG | AAC | TTC | TCC | GTT | ACC | ACC | TTC | AAC | 816 |
| Leu | Ala | Pro | Trp | Ala | Lys | Gly | Gln | Asn | Phe | Ser | Val | Thr | Thr | Phe | Asn |  |
|  |  |  | 260 |  |  |  |  | 265 |  |  |  |  | 270 |  |  |  |
| GGC | GGT | CTC | AAT | GAT | CAG | AAC | TCC | TCG | TCC | GAT | AGC | GGT | GAG | GCC | AAC | 864 |
| Gly | Gly | Leu | Asn | Asp | Gln | Asn | Ser | Ser | Ser | Asp | Ser | Gly | Glu | Ala | Asn |  |
|  |  | 275 |  |  |  |  | 280 |  |  |  |  | 285 |  |  |  |  |
| CTG | GAC | CTG | CAG | TAC | ATT | CTT | GGT | GTC | AGC | GCT | CCA | CTG | CCC | GTT | ACT | 912 |
| Leu | Asp | Leu | Gln | Tyr | Ile | Leu | Gly | Val | Ser | Ala | Pro | Leu | Pro | Val | Thr |  |
|  | 290 |  |  |  |  | 295 |  |  |  |  | 300 |  |  |  |  |  |
| GAA | TTC | AGC | ACC | GGA | GGC | CGT | GGT | CCC | CTC | GTT | CCT | GAT | CTG | ACC | CAG | 960 |
| Glu | Phe | Ser | Thr | Gly | Gly | Arg | Gly | Pro | Leu | Val | Pro | Asp | Leu | Thr | Gln |  |
| 305 |  |  |  |  | 310 |  |  |  |  | 315 |  |  |  |  | 320 |  |
| CCG | GAT | CCC | AAC | TCT | AAC | AGC | AAT | GAG | CCG | TAC | CTT | GAG | TTC | TTC | CAG | 1008 |
| Pro | Asp | Pro | Asn | Ser | Asn | Ser | Asn | Glu | Pro | Tyr | Leu | Glu | Phe | Phe | Gln |  |
|  |  |  |  | 325 |  |  |  |  | 330 |  |  |  |  | 335 |  |  |
| AAT | GTG | TTG | AAG | CTC | GAC | CAG | AAG | GAC | CTC | CCC | CAG | GTC | ATC | TCG | ACC | 1056 |
| Asn | Val | Leu | Lys | Leu | Asp | Gln | Lys | Asp | Leu | Pro | Gln | Val | Ile | Ser | Thr |  |
|  |  |  | 340 |  |  |  |  | 345 |  |  |  |  | 350 |  |  |  |
| TCC | TAT | GGA | GAG | AAC | GAA | CAG | GAA | ATC | CCC | GAA | AAG | TAC | GCT | CGC | ACC | 1104 |
| Ser | Tyr | Gly | Glu | Asn | Glu | Gln | Glu | Ile | Pro | Glu | Lys | Tyr | Ala | Arg | Thr |  |

```
                          355                           360                           365
     GTC  TGC  AAC  CTG  ATC  GCT  CAG  CTT  GGC  AGC  CGC  GGT  GTC  TCC  GTT  CTC    1152
     Val  Cys  Asn  Leu  Ile  Ala  Gln  Leu  Gly  Ser  Arg  Gly  Val  Ser  Val  Leu
          370                      375                      380

TTC  TCC  TCC  GGT  GAC  TCT  GGT  GTT  GGC  GAG  GGC  TGC  ATG  ACC  AAC  GAC    1200
     Phe  Ser  Ser  Gly  Asp  Ser  Gly  Val  Gly  Glu  Gly  Cys  Met  Thr  Asn  Asp
     385                      390                      395                      400

GGC  ACC  AAC  CGG  ACT  CAC  TTC  CCA  CCC  CAG  TTC  CCC  GCC  GCT  TGC  CCG    1248
     Gly  Thr  Asn  Arg  Thr  His  Phe  Pro  Pro  Gln  Phe  Pro  Ala  Ala  Cys  Pro
                         405                      410                      415

TGG  GTC  ACC  TCC  GTC  GGC  GCC  ACC  TTC  AAG  ACC  ACT  CCC  GAG  CGC  GGC    1296
     Trp  Val  Thr  Ser  Val  Gly  Ala  Thr  Phe  Lys  Thr  Thr  Pro  Glu  Arg  Gly
                    420                      425                      430

ACC  TAC  TTC  TCC  TCG  GGC  GGT  TTC  TCC  GAC  TAC  TGG  CCC  CGT  CCC  GAA    1344
     Thr  Tyr  Phe  Ser  Ser  Gly  Gly  Phe  Ser  Asp  Tyr  Trp  Pro  Arg  Pro  Glu
               435                      440                      445

TGG  CAG  GAT  GAG  GCC  GTG  AGC  AGC  TAC  CTC  GAG  ACG  ATC  GGC  GAC  ACT    1392
     Trp  Gln  Asp  Glu  Ala  Val  Ser  Ser  Tyr  Leu  Glu  Thr  Ile  Gly  Asp  Thr
          450                      455                      460

TTC  AAG  GGC  CTC  TAC  AAC  TCC  TCC  GGC  CGT  GCT  TTC  CCC  GAC  GTC  GCA    1440
     Phe  Lys  Gly  Leu  Tyr  Asn  Ser  Ser  Gly  Arg  Ala  Phe  Pro  Asp  Val  Ala
     465                      470                      475                      480

GCC  CAG  GGC  ATG  AAC  TTC  GCC  GTC  TAC  GAC  AAG  GGC  ACC  TTG  GGC  GAG    1488
     Ala  Gln  Gly  Met  Asn  Phe  Ala  Val  Tyr  Asp  Lys  Gly  Thr  Leu  Gly  Glu
                         485                      490                      495

TTC  GAC  GGC  ACC  TCC  GCC  TCC  GCC  CCG  GCC  TTC  AGC  GCC  GTC  ATC  GCT    1536
     Phe  Asp  Gly  Thr  Ser  Ala  Ser  Ala  Pro  Ala  Phe  Ser  Ala  Val  Ile  Ala
                    500                      505                      510

CTC  CTG  AAC  GAT  GCC  CGT  CTC  CGC  GCC  GGC  AAG  CCC  ACT  CTC  GGC  TTC    1584
     Leu  Leu  Asn  Asp  Ala  Arg  Leu  Arg  Ala  Gly  Lys  Pro  Thr  Leu  Gly  Phe
               515                      520                      525

CTG  AAC  CCC  TGG  TTG  TAC  AAG  ACC  GGC  CGC  CAG  GGT  CTG  CAA  GAT  ATC    1632
     Leu  Asn  Pro  Trp  Leu  Tyr  Lys  Thr  Gly  Arg  Gln  Gly  Leu  Gln  Asp  Ile
          530                      535                      540

ACC  CTC  GGT  GCT  AGC  ATT  GGC  TGC  ACC  GGT  CGC  GCT  CGC  TTC  GGC  GGC    1680
     Thr  Leu  Gly  Ala  Ser  Ile  Gly  Cys  Thr  Gly  Arg  Ala  Arg  Phe  Gly  Gly
     545                      550                      555                      560

GCC  CCT  GAC  GGT  GGT  CCC  GTC  GTG  CCT  TAC  GCT  AGC  TGG  AAC  GCT  ACC    1728
     Ala  Pro  Asp  Gly  Gly  Pro  Val  Val  Pro  Tyr  Ala  Ser  Trp  Asn  Ala  Thr
                         565                      570                      575

CAG  GGC  TGG  GAT  CCC  GTC  ACT  GGT  CTC  GGA  ACT  CCC  GAT  TTC  GCC  GAG    1776
     Gln  Gly  Trp  Asp  Pro  Val  Thr  Gly  Leu  Gly  Thr  Pro  Asp  Phe  Ala  Glu
                    580                      585                      590

CTC  AAG  AAG  CTT  GCC  CTT  GGC  AAC  TAA                                         1803
     Leu  Lys  Lys  Leu  Ala  Leu  Gly  Asn
               595                      600
```

(2) INFORMATION FOR SEQ ID NO:19:

(i) SEQUENCE CHARACTERISTICS:
        (A) LENGTH: 600 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:19:

```
Met  Phe  Phe  Ser  Arg  Gly  Ala  Leu  Ser  Leu  Ala  Val  Leu  Ser  Leu  Leu
  1                 5                       10                      15
```

| | | | | | | | | | | | | | | |
|---|---|---|---|---|---|---|---|---|---|---|---|---|---|---|
| Ser | Ser | Ser | Ala | Ala | Gly | Glu | Ala | Phe | Glu | Lys | Leu | Ser | Ala | Val | Pro |
| | | | 20 | | | | 25 | | | | | 30 | | | |
| Lys | Gly | Trp | His | Tyr | Ser | Ser | Thr | Pro | Lys | Gly | Asn | Thr | Glu | Val | Cys |
| | | 35 | | | | 40 | | | | | 45 | | | | |
| Leu | Lys | Ile | Ala | Leu | Ala | Gln | Lys | Asp | Ala | Ala | Gly | Phe | Glu | Lys | Thr |
| | 50 | | | | | 55 | | | | | 60 | | | | |
| Val | Leu | Glu | Met | Ser | Asp | Pro | Asp | His | Pro | Ser | Tyr | Gly | Gln | His | Phe |
| 65 | | | | | 70 | | | | 75 | | | | | | 80 |
| Thr | Thr | His | Asp | Glu | Met | Lys | Arg | Met | Leu | Leu | Pro | Arg | Asp | Asp | Thr |
| | | | | 85 | | | | | 90 | | | | | 95 | |
| Val | Asp | Ala | Val | Arg | Gln | Trp | Leu | Glu | Asn | Gly | Gly | Val | Thr | Asp | Phe |
| | | | 100 | | | | | 105 | | | | | 110 | | |
| Thr | Gln | Asp | Ala | Asp | Trp | Ile | Asn | Phe | Cys | Thr | Thr | Val | Asp | Thr | Ala |
| | | | 115 | | | | | 120 | | | | | 125 | | |
| Asn | Lys | Leu | Leu | Asn | Ala | Gln | Phe | Lys | Trp | Tyr | Val | Ser | Asp | Val | Lys |
| | 130 | | | | | 135 | | | | | 140 | | | | |
| His | Ile | Arg | Arg | Leu | Arg | Thr | Leu | Gln | Tyr | Asp | Val | Pro | Glu | Ser | Val |
| 145 | | | | | 150 | | | | | 155 | | | | | 160 |
| Thr | Pro | His | Ile | Asn | Thr | Ile | Gln | Pro | Thr | Arg | Phe | Gly | Lys | Ile |
| | | | | 165 | | | | | 170 | | | | | 175 |
| Ser | Pro | Lys | Lys | Ala | Val | Thr | His | Ser | Lys | Pro | Ser | Gln | Leu | Asp | Val |
| | | | | 180 | | | | | 185 | | | | | 190 | |
| Thr | Ala | Leu | Ala | Ala | Ala | Val | Val | Ala | Lys | Asn | Ile | Ser | His | Cys | Asp |
| | | | 195 | | | | | 200 | | | | | 205 | | |
| Ser | Ile | Ile | Thr | Pro | Thr | Cys | Leu | Lys | Glu | Leu | Tyr | Asn | Ile | Gly | Asp |
| | | 210 | | | | | 215 | | | | | 220 | | | |
| Tyr | Gln | Ala | Asp | Ala | Asn | Ser | Gly | Ser | Lys | Ile | Ala | Phe | Ala | Ser | Tyr |
| 225 | | | | | 230 | | | | | 235 | | | | | 240 |
| Leu | Glu | Glu | Tyr | Ala | Arg | Tyr | Ala | Asp | Leu | Glu | Asn | Phe | Glu | Asn | Tyr |
| | | | | 245 | | | | | 250 | | | | | 255 | |
| Leu | Ala | Pro | Trp | Ala | Lys | Gly | Gln | Asn | Phe | Ser | Val | Thr | Thr | Phe | Asn |
| | | | | 260 | | | | 265 | | | | | 270 | | |
| Gly | Gly | Leu | Asn | Asp | Gln | Asn | Ser | Ser | Asp | Ser | Gly | Glu | Ala | Asn |
| | | | 275 | | | | | 280 | | | | | 285 | | |
| Leu | Asp | Leu | Gln | Tyr | Ile | Leu | Gly | Val | Ser | Ala | Pro | Leu | Pro | Val | Thr |
| | 290 | | | | | 295 | | | | | 300 | | | | |
| Glu | Phe | Ser | Thr | Gly | Gly | Arg | Gly | Pro | Leu | Val | Pro | Asp | Leu | Thr | Gln |
| 305 | | | | | 310 | | | | | 315 | | | | | 320 |
| Pro | Asp | Pro | Asn | Ser | Asn | Ser | Asn | Glu | Pro | Tyr | Leu | Glu | Phe | Phe | Gln |
| | | | | 325 | | | | | 330 | | | | | 335 | |
| Asn | Val | Leu | Lys | Leu | Asp | Gln | Lys | Asp | Leu | Pro | Gln | Val | Ile | Ser | Thr |
| | | | 340 | | | | | 345 | | | | | 350 | | |
| Ser | Tyr | Gly | Glu | Asn | Glu | Gln | Glu | Ile | Pro | Glu | Lys | Tyr | Ala | Arg | Thr |
| | | 355 | | | | | 360 | | | | | 365 | | | |
| Val | Cys | Asn | Leu | Ile | Ala | Gln | Leu | Gly | Ser | Arg | Gly | Val | Ser | Val | Leu |
| | 370 | | | | | 375 | | | | | 380 | | | | |
| Phe | Ser | Ser | Gly | Asp | Ser | Gly | Val | Gly | Glu | Gly | Cys | Met | Thr | Asn | Asp |
| 385 | | | | | 390 | | | | | 395 | | | | | 400 |
| Gly | Thr | Asn | Arg | Thr | His | Phe | Pro | Pro | Gln | Phe | Pro | Ala | Ala | Cys | Pro |
| | | | | 405 | | | | | 410 | | | | | 415 | |
| Trp | Val | Thr | Ser | Val | Gly | Ala | Thr | Phe | Lys | Thr | Pro | Glu | Arg | Gly |
| | | | 420 | | | | | 425 | | | | | 430 | | |
| Thr | Tyr | Phe | Ser | Ser | Gly | Gly | Phe | Ser | Asp | Tyr | Trp | Pro | Arg | Pro | Glu |
| | | | 435 | | | | | 440 | | | | | 445 | | |

| | | | | | | | | | | | | | | |
|---|---|---|---|---|---|---|---|---|---|---|---|---|---|---|
| Trp | Gln | Asp | Glu | Ala | Val | Ser | Ser | Tyr | Leu | Glu | Thr | Ile | Gly | Asp | Thr |
| | 450 | | | | | 455 | | | | | 460 | | | | |
| Phe | Lys | Gly | Leu | Tyr | Asn | Ser | Ser | Gly | Arg | Ala | Phe | Pro | Asp | Val | Ala |
| 465 | | | | | 470 | | | | | 475 | | | | | 480 |
| Ala | Gln | Gly | Met | Asn | Phe | Ala | Val | Tyr | Asp | Lys | Gly | Thr | Leu | Gly | Glu |
| | | | | 485 | | | | | 490 | | | | | 495 | |
| Phe | Asp | Gly | Thr | Ser | Ala | Ser | Ala | Pro | Ala | Phe | Ser | Ala | Val | Ile | Ala |
| | | | 500 | | | | | 505 | | | | | 510 | | |
| Leu | Leu | Asn | Asp | Ala | Arg | Leu | Arg | Ala | Gly | Lys | Pro | Thr | Leu | Gly | Phe |
| | | | 515 | | | | 520 | | | | | 525 | | | |
| Leu | Asn | Pro | Trp | Leu | Tyr | Lys | Thr | Gly | Arg | Gln | Gly | Leu | Gln | Asp | Ile |
| | | 530 | | | | 535 | | | | | 540 | | | | |
| Thr | Leu | Gly | Ala | Ser | Ile | Gly | Cys | Thr | Gly | Arg | Ala | Arg | Phe | Gly | Gly |
| 545 | | | | | 550 | | | | | 555 | | | | | 560 |
| Ala | Pro | Asp | Gly | Gly | Pro | Val | Val | Pro | Tyr | Ala | Ser | Trp | Asn | Ala | Thr |
| | | | | 565 | | | | | 570 | | | | | 575 | |
| Gln | Gly | Trp | Asp | Pro | Val | Thr | Gly | Leu | Gly | Thr | Pro | Asp | Phe | Ala | Glu |
| | | | 580 | | | | | 585 | | | | | 590 | | |
| Leu | Lys | Lys | Leu | Ala | Leu | Gly | Asn | | | | | | | | |
| | | 595 | | | | | 600 | | | | | | | | |

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TAYAAYATHG GGAYTAYCAR GCYGAYGC 28

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GCACGCYTGR TTYTGCCAYT CGG 23

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GGGATTTAAA TATGTTCTTC AGTCGT 26

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:23:

GGGTTAATTA ATTAGTTGCC AAGGGC 2 6